United States Patent
Sato et al.

(10) Patent No.: US 11,180,554 B2
(45) Date of Patent: Nov. 23, 2021

(54) ANTI-HUMAN CD73 ANTIBODY

(71) Applicant: Astellas Pharma Inc., Tokyo (JP)

(72) Inventors: Masahito Sato, Tokyo (JP); Hanae Toyonaga, Tokyo (JP); Fumio Osaki, Tokyo (JP); Tomohiro Eguchi, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 243 days.

(21) Appl. No.: 16/469,096

(22) PCT Filed: Dec. 12, 2017

(86) PCT No.: PCT/JP2017/044578
§ 371 (c)(1),
(2) Date: Jun. 12, 2019

(87) PCT Pub. No.: WO2018/110555
PCT Pub. Date: Jun. 21, 2018

(65) Prior Publication Data
US 2020/0071404 A1    Mar. 5, 2020

(30) Foreign Application Priority Data
Dec. 13, 2016 (JP) ............................. JP2016-241503

(51) Int. Cl.
*C07K 16/28* (2006.01)
*A61K 45/06* (2006.01)

(52) U.S. Cl.
CPC ...... *C07K 16/2806* (2013.01); *C07K 16/2896* (2013.01); *A61K 45/06* (2013.01); *C07K 2317/24* (2013.01); *C07K 2317/33* (2013.01); *C07K 2317/565* (2013.01); *C07K 2317/622* (2013.01); *C07K 2317/71* (2013.01); *C07K 2317/92* (2013.01)

(58) Field of Classification Search
None
See application file for complete search history.

(56) References Cited

FOREIGN PATENT DOCUMENTS

| WO | WO-2016/055609 A1 | 4/2016 |
| WO | WO-2016/075176 A1 | 5/2016 |
| WO | WO-2016/081748 A2 | 5/2016 |

OTHER PUBLICATIONS

Office Action dated Jan. 13, 2021 in corresponding Russian application No. 2019118359, with English translation.
Supplementary European Search Report dated Jul. 20, 2020, in EP 17881964.5.
Geoghegan et al., "Inhibition of CD73 AMP hydrolysis by a therapeutic antibody with a dual, non-competitive mechanism of action," mAbs, 2016, 8(3):454-467.
International Search Report dated Mar. 6, 2018, in PCT/JP2017/044578.

*Primary Examiner* — Adam Weidner
(74) *Attorney, Agent, or Firm* — Foley & Lardner LLP

(57) ABSTRACT

[Problem] Provided is an anti-human CD73 antibody which is enhanced as compared to the antibody in the prior art and has an ability of recovering AMP-dependently suppressed T cell functions.
[Means for Solution] Provided is an anti-human CD73 antibody comprising a heavy chain variable region comprising CDR1 consisting of the amino acid sequence of amino acid numbers 31 to 35 of SEQ ID NO: 2, CDR2 consisting of the amino acid sequence of amino acid numbers 50 to 66 of SEQ ID NO: 2, and CDR3 consisting of the amino acid sequence of amino acid numbers 99 to 112 of SEQ ID NO: 2, and a light chain variable region comprising CDR1 consisting of the amino acid sequence of amino acid numbers 24 to 34 of SEQ ID NO: 4, CDR2 consisting of the amino acid sequence of amino acid numbers 50 to 56 of SEQ ID NO: 4, and CDR3 consisting of the amino acid sequence of amino acid numbers 89 to 98 of SEQ ID NO: 4.

25 Claims, 2 Drawing Sheets
Specification includes a Sequence Listing.

ANTI-HUMAN CD73 ANTIBODY

CROSS-REFERENCE TO RELATED APPLICATIONS

This application is a National Stage application of PCT/JP2017/044578, filed Dec. 12, 2017, which claims priority from Japanese application JP 2016-241503, filed Dec. 13, 2016.

The instant application contains a Sequence Listing which has been submitted in ASCII format via EFS-WEB and is hereby incorporated by reference in its entirety. Said ASCII copy, created on Jun. 8, 2019, is named sequence.txt and is 70,833 bytes.

TECHNICAL FIELD

The present invention relates to an anti-human CD73 antibody which is useful as an active ingredient of a pharmaceutical composition.

BACKGROUND ART

CD73 (Ecto-5'-nucleotidase) is an enzyme which catalyzes the decomposition of AMP (adenosine monophosphate) into adenosine. CD73 is a GPI anchor-type protein, present on a cell membrane surface as a dimer, and is expressed in various tissues such as lymphocytic cells, endothelial cells, the large intestine, the brain, the kidney, the liver, the lungs, the heart, and the like. In addition, it has been reported that CD73 is cut from a cell membrane surface of a lymphocytic cell and is present as soluble CD73, and the soluble CD73 also has an enzymatic activity of decomposing AMP. Since adenosine which is produced by the decomposition of AMP suppresses functions of immune system cells such as T cells, CD73 plays an important role in adjusting immune response (Arterioscler Thromb Vasc Biol., Vol. 28, p. 18-26, 2008) (Trends Mol Med., Vol. 19, p. 355-367, 2013) (Eur J Immunol., Vol. 45, p. 562-573, 2015).

As for the relation to a disease state, it has been confirmed that CD73 is expressed at a colon cancer cell line (Mediators Inflamm., Article ID 879895, 2014). In addition, it has been reported that in a colon cancer patient, expression of CD73 is increased in cancer tissues than in normal tissues, and a patient with high CD73 expression has a lower overall survival rate than a patient with low CD73 expression (J Surg Oncol., Vol. 106, p. 130-137, 2012).

With regard to other kinds of cancers, it has been confirmed that CD73 is expressed in cell lines of adrenal cancer, breast cancer, malignant melanoma, glioblastoma multiforme, ovarian cancer, medulloblastoma, and bladder cancer, and CD73 activity is increased in breast cancer, stomach cancer, pancreatic cancer, chronic myeloid leukemia, cutaneous T-cell lymphoma, and glioblastoma (Pharmacol Ther., Vol. 87, p. 161-173, 2000) (Biomed Res Int., Article ID 460654, 2014). In addition, it has been reported that expression of CD73 is increased in head and neck cancer and thyroid cancer, or expression of CD73 accelerates proliferation of cancer cells in prostate cancer (Trends Mol Med., Vol. 19, p. 355-367, 2013).

Inhibition of the enzymatic activity of CD73 which decomposes AMP is associated with activation of anti-tumor immunity by recovering suppressed functions of immune system cells such as a T cell, and thus CD73 is studied as a treatment target for cancer. In addition, it has been known that an anti-CD73 antibody having such an enzyme inhibitory activity shows an anti-tumor activity in animal models (Non-Patent Document 1).

A plurality of studies is carried out regarding an antibody which inhibits an enzymatic activity of human CD73 (Patent Document 1, Patent Document 2, Patent Document 3, and Non-Patent Document 1). MEDI9447 reported in Patent Document 1 and Non-Patent Document 1 has characteristics of showing bell-shaped inhibition against soluble CD73. Although a phase I trial has been started on MEDI9447 with solid-type cancers being adapted cancers, the clinical treatment effect has yet to be confirmed, even including antibodies reported in Patent Document 2 and Patent Document 3.

A fused form of an antibody or an antigen-binding fragment thereof and a cytokine, which is called immunocytokine, is known, and a plurality of studies is carried out on the purpose of activating anti-tumor immunity (Curr Opinion in Immunol., Vol. 40, p. 96-102, 2016).

As examples of cytokine which has a possibility of activating anti-tumor immunity, studies on IL-7 and IL-21 are carried out, but it is reported that IL-7 and IL-21 have a possibility of showing toxicity when high doses of IL-7 and IL-21 are administered to a human (Clin Cancer Res., Vol. 16, p. 727-735, 2010) (Clin Cancer Res., Vol. 13, p. 3630-3636, 2007).

RELATED ART

Patent Document

[Patent Document 1] WO 2016/075176
[Patent Document 2] WO 2016/055609
[Patent Document 3] WO 2016/081748

Non-Patent Document

[Non-Patent Document 1] "mAbs" (USA), 8 (3); 454-467, 2016

DISCLOSURE OF INVENTION

Problems to be Solved by the Invention

An object of the present invention is to provide an anti-human CD73 antibody.

Means for Solving the Problems

As a result of performing intensive creative research on preparation of an anti-human CD73 antibody by the present inventors, an anti-human CD73 antibody CDS-1 that comprises a heavy chain variable region comprising CDR1 consisting of the amino acid sequence of amino acid numbers 31 to 35 of SEQ ID NO: 2, CDR2 consisting of the amino acid sequence of amino acid numbers 50 to 66 of SEQ ID NO: 2, and CDR3 consisting of the amino acid sequence of amino acid numbers 99 to 112 of SEQ ID NO: 2, and a light chain variable region comprising CDR1 consisting of the amino acid sequence of amino acid numbers 24 to 34 of SEQ ID NO: 4, CDR2 consisting of the amino acid sequence of amino acid numbers 50 to 56 of SEQ ID NO: 4, and CDR3 consisting of the amino acid sequence of amino acid numbers 89 to 98 of SEQ ID NO: 4 (Example 1) was prepared, and it was found that the antibody binds to human CD73 (Example 2), inhibits an enzymatic activity of human CD73 (Examples 3 and 4), and recovers AMP-dependently suppressed human T cell functions (Example 5). As a result, the above-described anti-human CD73 antibody of the present invention is provided, thereby completing the present invention.

That is, the present invention relates to the following [1] to [31].

[1]
An anti-human CD73 antibody or an antigen-binding fragment thereof comprising:
a heavy chain variable region comprising CDR1 consisting of the amino acid sequence of amino acid numbers 31 to 35 of SEQ ID NO: 2, CDR2 consisting of the amino acid sequence of amino acid numbers of 50 to 66 of SEQ ID NO: 2, and CDR3 consisting of the amino acid sequence of amino acid numbers of 99 to 112 of SEQ ID NO: 2; and
a light chain variable region comprising CDR1 consisting of the amino acid sequence of amino acid numbers of 24 to 34 of SEQ ID NO: 4, CDR2 consisting of the amino acid sequence of amino acid numbers of 50 to 56 of SEQ ID NO: 4, and CDR3 consisting of the amino acid sequence of amino acid numbers of 89 to 98 of SEQ ID NO: 4.

[2]
The anti-human CD73 antibody or the antigen-binding fragment thereof described in [1], comprising a heavy chain variable region consisting of the amino acid sequence of amino acid numbers of 1 to 123 of SEQ ID NO: 2, and a light chain variable region consisting of the amino acid sequence of amino acid numbers of 1 to 109 of SEQ ID NO: 4.

[3]
The anti-human CD73 antibody described in [1] or [2], selected from the group consisting of the following (a) and (b):
(a) an anti-human CD73 antibody comprising a heavy chain consisting of the amino acid sequence shown by SEQ ID NO: 2 and a light chain consisting of the amino acid sequence shown by SEQ ID NO: 4; and
(b) an anti-human CD73 antibody which is derived from posttranslational modification of the anti-human CD73 antibody of (a).

[4]
The anti-human CD73 antibody described in [3], selected from the group consisting of the following (a) and (b):
(a) an anti-human CD73 antibody comprising the heavy chain consisting of the amino acid sequence shown by SEQ ID NO: 2 and the light chain consisting of the amino acid sequence shown by SEQ ID NO: 4; and
(b) an anti-human CD73 antibody comprising a heavy chain consisting of the amino acid sequence of amino acid numbers of 1 to 452 of SEQ ID NO: 2 and the light chain consisting of the amino acid sequence shown by SEQ ID NO: 4.

[5]
The anti-human CD73 antibody described in [4], comprising the heavy chain consisting of the amino acid sequence shown by SEQ ID NO: 2, and the light chain consisting of the amino acid sequence shown by SEQ ID NO: 4.

[6]
The anti-human CD73 antibody described in [4], comprising the heavy chain consisting of the amino acid sequence of amino acid numbers of 1 to 452 of SEQ ID NO: 2, and the light chain consists of the amino acid sequence shown by SEQ ID NO: 4.

[7]
A fused form in which the anti-human CD73 antibody or the antigen-binding fragment thereof described in any one of [1] to [6] is fused with another peptide or protein.

[8]
A modified form in which the anti-human CD73 antibody or the antigen-binding fragment thereof described in any one of [1] to [6] binds to a modifying agent.

[9]
The fused form described in [7], selected from the group consisting of the following (a) to (e):
(a) a fused form comprising a heavy chain consisting of the amino acid sequence shown by SEQ ID NO: 7 and a light chain consisting of the amino acid sequence shown by SEQ ID NO: 4;
(b) a fused form comprising a heavy chain consisting of the amino acid sequence shown by SEQ ID NO: 10 and a light chain consisting of the amino acid sequence shown by SEQ ID NO: 4;
(c) a fused form comprising a heavy chain consisting of the amino acid sequence shown by SEQ ID NO: 2 and a light chain consisting of the amino acid sequence shown by SEQ ID NO: 13;
(d) a fused form comprising a heavy chain consisting of the amino acid sequence shown by SEQ ID NO: 2 and a light chain consisting of the amino acid sequence shown by SEQ ID NO: 15; and
(e) a fused form which is derived from posttranslational modifications of the fused forms of (a) to (d).

[10]
A polynucleotide selected from the group consisting of the following (a) and (b):
(a) a polynucleotide comprising a sequence encoding a heavy chain variable region of the antibody or the antigen-binding fragment thereof described in [2]; and
(b) a polynucleotide comprising a sequence encoding a light chain variable region of the antibody or the antigen-binding fragment thereof described in [2].

[11]
The polynucleotide described in [10], selected from the group consisting of the following (a) and (b):
(a) a polynucleotide comprising a sequence encoding a heavy chain of the antibody described in [5]; and
(b) a polynucleotide comprising a sequence encoding a light chain of the antibody described in [5].

[12]
The polynucleotide described in [11], selected from the group consisting of the following (a) and (b):
(a) a polynucleotide comprising a sequence encoding a heavy chain of the fused form described in [9]; and
(b) a polynucleotide comprising a sequence encoding a light chain of the fused form described in [9].

[13]
An expression vector comprising the following (a) and/or (b):
(a) a polynucleotide comprising a sequence encoding a heavy chain variable region of the antibody or the antigen-binding fragment thereof described in [2]; and
(b) a polynucleotide comprising a sequence encoding a light chain variable region of the antibody or the antigen-binding fragment thereof described in [2].

[14]
The expression vector described in [13], comprising the following (a) and/or (b):
(a) a polynucleotide comprising a sequence encoding a heavy chain of the antibody described in [5]; and
(b) a polynucleotide comprising a sequence encoding a light chain of the antibody described in [5].

[15]
The expression vector described in [14], comprising the following (a) and/or (b):
(a) a polynucleotide comprising a sequence encoding a heavy chain of the fused form described in [9]; and
(b) a polynucleotide comprising a sequence encoding a light chain of the fused form described in [9].

[16]
A host cell selected from the group consisting of the following (a) to (d):
(a) a host cell transformed with an expression vector comprising a polynucleotide comprising a sequence encoding a heavy chain variable region of the antibody or the antigen-binding fragment thereof described in [2];
(b) a host cell transformed with an expression vector comprising a polynucleotide comprising a sequence encoding a light chain variable region of the antibody or the antigen-binding fragment thereof described in [2];
(c) a host cell transformed with an expression vector comprising a polynucleotide comprising a sequence encoding a heavy chain variable region of the antibody or the antigen-binding fragment thereof described in [2] and a polynucleotide comprising a sequence encoding a light chain variable region of the antibody or the antigen-binding fragment thereof described in [2]; and
(d) a host cell transformed with an expression vector comprising a polynucleotide comprising a sequence encoding a heavy chain variable region of the antibody or the antigen-binding fragment thereof described in [2] and an expression vector comprising a polynucleotide comprising a sequence encoding a light chain variable region of the antibody or the antigen-binding fragment thereof described in [2].

[17]
The host cell described in [16], selected from the group consisting of the following (a) to (d):
(a) a host cell transformed with an expression vector comprising a polynucleotide comprising a sequence encoding a heavy chain of the antibody described in [5];
(b) a host cell transformed with an expression vector comprising a polynucleotide comprising a sequence encoding a light chain of the antibody described in [5];
(c) a host cell transformed with an expression vector comprising a polynucleotide comprising a sequence encoding a heavy chain of the antibody described in [5] and a polynucleotide comprising a sequence encoding a light chain of the antibody described in [5]; and
(d) a host cell transformed with an expression vector comprising a polynucleotide comprising a sequence encoding a heavy chain of the antibody described in [5] and an expression vector comprising a polynucleotide comprising a sequence encoding a light chain of the antibody described in [5].

[18]
The host cell described in [17], selected from the group consisting of the following (a) to (d):
(a) a host cell transformed with an expression vector comprising a polynucleotide comprising a sequence encoding a heavy chain of the fused form described in [9];
(b) a host cell transformed with an expression vector comprising a polynucleotide comprising a sequence encoding a light chain of the fused form described in [9];
(c) a host cell transformed with an expression vector comprising a polynucleotide comprising a sequence encoding a heavy chain of the fused form described in [9] and a polynucleotide comprising a sequence encoding a light chain of the fused form described in [9]; and
(d) a host cell transformed with an expression vector comprising a polynucleotide comprising a sequence encoding a heavy chain of the fused form described in [9] and an expression vector comprising a polynucleotide comprising a sequence encoding a light chain of the fused form described in [9].

[19]
A method for producing an anti-human CD73 antibody, an antigen-binding fragment thereof, or a fused form of any one thereof, the method comprising:
culturing a host cell selected from the group consisting of the following (a) to (c) to express an anti-human CD73 antibody, an antigen-binding fragment thereof, or a fused form of any one thereof:
(a) a host cell transformed with an expression vector comprising a polynucleotide comprising a base sequence encoding a heavy chain variable region of the antibody or the antigen-binding fragment thereof described in [2] and a polynucleotide comprising a base sequence encoding a light chain variable region of the antibody or the antigen-binding fragment thereof described in [2];
(b) a host cell transformed with an expression vector comprising a polynucleotide comprising a base sequence encoding a heavy chain variable region of the antibody or the antigen-binding fragment thereof described in [2] and an expression vector comprising a polynucleotide comprising a base sequence encoding a light chain variable region of the antibody or the antigen-binding fragment thereof described in [2]; and
(c) a host cell transformed with an expression vector comprising a polynucleotide comprising a base sequence encoding a heavy chain variable region of the antibody or the antigen-binding fragment thereof described in [2] and a host cell transformed with an expression vector comprising a polynucleotide comprising a base sequence encoding a light chain variable region of the antibody or the antigen-binding fragment thereof described in [2].

[20]
A method for producing an anti-human CD73 antibody or a fused form thereof, comprising:
culturing a host cell selected from the group consisting of the following (a) to (c) to express an anti-human CD73 antibody or a fused form thereof:
(a) a host cell transformed with an expression vector comprising a polynucleotide comprising a base sequence encoding a heavy chain of the antibody described in [5] and a polynucleotide comprising a base sequence encoding a light chain of the antibody described in [5];
(b) a host cell transformed with an expression vector comprising a polynucleotide comprising a base sequence encoding a heavy chain of the antibody described in [5] and an expression vector comprising a polynucleotide comprising a base sequence encoding a light chain of the antibody described in [5]; and
(c) a host cell transformed with an expression vector comprising a polynucleotide comprising a base sequence encoding a heavy chain of the antibody described in [5] and a host cell transformed with an expression vector comprising a polynucleotide comprising a base sequence encoding a light chain of the antibody described in [5].

[21]
A method for producing a fused form of an anti-human CD73 antibody comprising:
culturing a host cell selected from the group consisting of the following (a) to (c) to express a fused form of an anti-human CD73 antibody:

(a) a host cell transformed with an expression vector comprising a polynucleotide comprising a base sequence encoding a heavy chain of the fused form described in [9] and a polynucleotide comprising a base sequence encoding a light chain of the fused form described in [9];

(b) a host cell transformed with an expression vector comprising a polynucleotide comprising a base sequence encoding a heavy chain of the fused form described in [9] and an expression vector comprising a polynucleotide comprising a base sequence encoding a light chain of the fused form described in [9]; and (c) a host cell transformed with an expression vector comprising a polynucleotide comprising a base sequence encoding a heavy chain of the fused form described in [9] and a host cell transformed with an expression vector comprising a polynucleotide comprising a base sequence encoding a light chain of the fused form described in [9].

[22]
A pharmaceutical composition comprising the anti-human CD73 antibody described in [3], and a pharmaceutically acceptable excipient.

[23]
The pharmaceutical composition described in [22], which is a pharmaceutical composition for preventing or treating cancer.

[24]
A method for preventing or treating cancer, comprising administering a therapeutically effective amount of the anti-human CD73 antibody described in [3].

[25]
The anti-human CD73 antibody described in [3], which is for use in preventing or treating cancer.

[26]
Use of the anti-human CD73 antibody described in [3] for the manufacture of a pharmaceutical composition for preventing or treating cancer.

[27]
A pharmaceutical composition comprising the fused form described in [9], and a pharmaceutically acceptable excipient.

[28]
The pharmaceutical composition described in [27], which is a pharmaceutical composition for preventing or treating cancer.

[29]
A method for preventing or treating cancer, comprising administering a therapeutically effective amount of the fused form described in [9].

[30]
The fused form described in [9] for use in preventing or treating cancer.

[31]
Use of the fused form described in [9] for the manufacture of a pharmaceutical composition for preventing or treating cancer.

Effects of the Invention

The anti-human CD73 antibody of the present invention has an activity of inhibiting human CD73 enzymatic activity and can be used as an agent for preventing or treating cancer.

EMBODIMENTS FOR CARRYING OUT THE INVENTION

Figure 1:
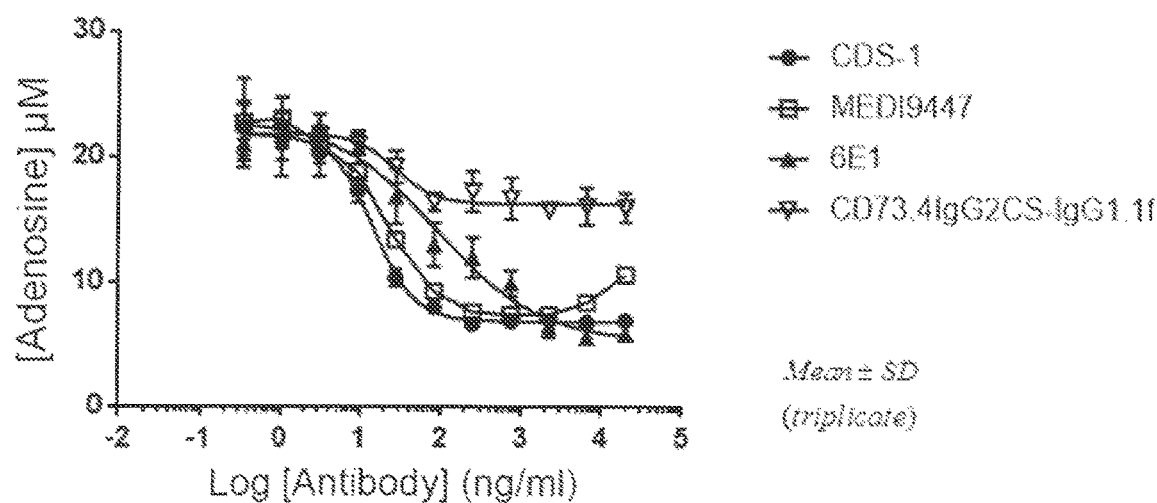
FIG. 1 is a view illustrating enzyme inhibitory activity of CDS-1, MEDI9447, 6E1, and CD73.4IgG2CS-IgG1.1f to human CD73 protein.

Hereinafter, the present invention will be described in detail.

There are five classes of IgG, IgM, IgA, IgD, and IgE in an antibody. The basic structure of an antibody molecule is configured of heavy chains having a molecular weight of 50000 to 70000 and light chains having a molecular weight of 20000 to 30000 in each of the classes in common. Heavy chain usually consists of a polypeptide chain comprising approximately 440 amino acids, has a distinctive structure for each of the classes, and is referred to as Igγ, Igμ, Igα, Igδ, and Igε corresponding to IgG, IgM, IgA, IgD, and IgE, respectively. Further, four subclasses of IgG1, IgG2, IgG3, and IgG4 are present in IgG and the heavy chains respectively corresponding thereto are referred to as Igγ1, Igγ2, Igγ3, and Igγ4. Light chain usually consists of a polypeptide chain comprising 220 amino acids, two types of which, type L and type K are known, and are referred to as Igλ, and Igκ. In a peptide configuration of the basic structure of antibody molecules, two homologous heavy chains and two homologous light chains are bound by disulfide bonds (S—S bond) and non-covalent bonds, and the molecular weight thereof is 150000 to 190000. Two kinds of light chains can be paired with any heavy chain. The respective antibody molecules typically consist of two identical light chains and two identical heavy chains.

With regard to intrachain S—S bonds, four of the S—S bonds are present in the heavy chain (five in μ and ε chains) and two of them are present in the light chain; one loop is formed per 100 to 110 amino acid residues, and this steric structure is similar among the loops and are referred to as a structural unit or a domain. The domain located at the amino terminal side (N terminal side) in both of the heavy chain and the light chain, whose amino acid sequence is not constant even in a case of a sample from the same class (sub class) of the same kind of animal is referred to as a variable region, and respective domains are referred to as a heavy chain variable region (or VH) and a light chain variable region (or VL). The amino acid sequence of the carboxy terminal side (C terminal side) from the variable region is nearly constant in each class or subclass and is referred to as a constant region. Respective domains of the constant region are represented as CH1, CH2, CH3, or CL in order from the variable region side, respectively.

An antigenic binding site of an antibody is configured of VH and VL, and the binding specificity depends on the amino acid sequence of this site. On the other hand, biological activities such as binding to complements and various effector cells reflect differences in the constant region structures among each class Ig. It is understood that the variability of variable regions of the light chains and the heavy chains is mostly limited to three small hypervariable regions present in both chains and these regions are referred to as complementarity determining regions (CDR: CDR1, CDR2, and CDR3 from the N terminal side). The remaining portion of the variable region is referred to as a framework region (FR) and is relatively constant.

Various antigen-binding fragments comprising VH and VL of an antibody also have antigen-binding activities, and representative examples of such an antigen-binding fragment include a single chain variable region fragment (scFv), Fab, Fab', and F(ab')$_2$. Fab is a monovalent antibody fragment which is configured of a light chain and a heavy chain fragment comprising VH, a CH1 domain, and a portion of a hinge region. Fab' is a monovalent antibody fragment which is configured of a light chain and a heavy chain fragment comprising VH, a CH1 domain, and a portion of a hinge region, and the portion of the hinge region includes cysteine residues configuring the S—S bond between heavy chains. F(ab')$_2$ fragment is a divalent antibody fragment in which two Fab' fragments are bound by an S—S bond between heavy chains in the hinge region. In addition, scFv is a monovalent antibody fragment which is configured of VH and VL connected to each other via a linker.

With the designation of the Kabat numbering or the EU index (Kabat et al. Sequences of Proteins of Immunological Interest, Fifth Edition, NIH Publication No. 91-3242, 1991), the amino acid residue number of the antibody used in the present specification can be defined according to the numbering system.

<Anti-Human CD73 Antibody of the Present Invention>

The anti-human CD73 antibody of the present invention includes an anti-human CD73 antibody or an antigen-binding fragment thereof having the following characteristics.

An anti-human CD73 antibody or an antigen-binding fragment thereof comprising a heavy chain variable region comprising CDR1 consisting of the amino acid sequence of amino acid numbers 31 to 35 of SEQ ID NO: 2, CDR2 consisting of the amino acid sequence of amino acid numbers 50 to 66 of SEQ ID NO: 2, and CDR3 consisting of the amino acid sequence of amino acid numbers 99 to 112 of SEQ ID NO: 2 and a light chain variable region comprising CDR1 consisting of the amino acid sequence of amino acid numbers 24 to 34 of SEQ ID NO: 4, CDR2 consisting of the amino acid sequence of amino acid numbers 50 to 56 of SEQ ID NO: 4, and CDR3 consisting of the amino acid sequence of amino acid numbers 89 to 98 of SEQ ID NO: 4.

In one embodiment, the anti-human CD73 antibody of the present invention includes the following anti-human CD73 antibody or the antigen-binding fragment thereof:

an anti-human CD73 antibody or an antigen-binding fragment thereof comprising a heavy chain variable region consisting of the amino acid sequence of amino acid numbers 1 to 123 of SEQ ID NO: 2 and a light chain variable region consisting of the amino acid sequence of amino acid numbers 1 to 109 of SEQ ID NO: 4.

As the heavy chain constant region of the anti-human CD73 antibody of the present invention, any constant region of Igγ, Igμ, Igα, Igδ, or Igε can be selected. For example, Igγ can be selected from Igγ1, Igγ2, Igγ3, or Igγ4. As one embodiment, the heavy chain constant region is an Igγ1 constant region. For example, the heavy chain constant region is a human Igγ1 constant region.

The heavy chain constant region of the anti-human CD73 antibody of the present invention may have mutations for the purpose of degrading an antibody-dependent cellular cytotoxicity activity or a complement-dependent cytotoxicity activity of an antibody. L234A is a substitution of leucine at the amino acid 234 position with alanine in the human Igγ1 constant region according to the EU index. L235A is a substitution of leucine at the amino acid 235 position with alanine in the human Igγ1 constant region according to the EU index. P331S is a substitution of proline at the amino acid 331 position with serine in the human Igγ1 constant region according to the EU index. Examples of the human Igγ1 constant region having amino mutations of L234A, L235A, and P331S include a human Igγ1 constant region consisting of the amino acid sequence of amino acid numbers 124 to 453 of SEQ ID NO: 2. It is known that the mutations degrade the antibody-dependent cellular cytotoxicity activity or the complement-dependent cytotoxicity activity of an antibody (Mol Immunol., Vol. 29, p. 633-639, 1992) (J Immunol., Vol. 164, p. 4178-4184, 2000).

As the light chain constant region of the anti-human CD73 antibody of the present invention, any constant region of Igλ or Igκ can be selected. As one embodiment, the light chain constant region is a Igκ constant region. For example, the light chain constant region is a human Igκ constant region. Examples of the human Igκ constant region include a human Igκ constant region consisting of the amino acid sequence of amino acid numbers 110 to 215 of SEQ ID NO: 4.

In one embodiment, the anti-human CD73 antibody of the present invention is an antigen-binding fragment which is scFv, Fab, Fab', or F(ab')$_2$.

In one embodiment, the anti-human CD73 antibody of the present invention is an anti-human CD73 antibody comprising a heavy chain consisting of the amino acid sequence shown by SEQ ID NO: 2 and a light chain consisting of the amino acid sequence shown by SEQ ID NO: 4.

It is known that when an antibody is expressed in cells, the antibody is modified after translation. Examples of the posttranslational modification include cleavage of lysine at the C terminal of the heavy chain by a carboxypeptidase; modification of glutamine or glutamic acid at the N terminal of the heavy chain and the light chain to pyroglutamic acid by pyroglutamylation; glycosylation; oxidation; deamidation; and glycation, and it is known that such posttranslational modifications occur in various antibodies (Journal of Pharmaceutical Sciences, Vol. 97, p. 2426-2447, 2008).

The anti-human CD73 antibody of the present invention includes an anti-human CD73 antibody which is an antibody derived from posttranslational modification or an antigen-binding fragment thereof. The antibody which is derived from posttranslational modification includes an antibody comprising polypeptide consisting of the amino acid sequence of the antibody derived from posttranslational modification. Examples of the anti-human CD73 antibody of the present invention which is an antibody derived from posttranslational modification include anti-human CD73 antibodies which have undergone pyroglutamylation at the N terminal of the heavy chain variable region and/or deletion of lysine at the C terminal of the heavy chain. It is known in the field that such posttranslational modification due to pyroglutamylation at the N terminal and deletion of lysine at the C terminal does not have any influence on the activity of the antibody (Analytical Biochemistry, Vol. 348, p. 24-39, 2006).

In one embodiment, the anti-human CD73 antibody of the present invention which is derived from posttranslational modification is the following anti-human CD73 antibody:

an anti-human CD73 antibody comprising a heavy chain consisting of the amino acid sequence of amino acid numbers 1 to 452 of SEQ ID NO: 2 and a light chain consisting of the amino acid sequence shown by SEQ ID NO: 4.

In the present specification, the "anti-human CD73 antibody" means an antibody binding to human CD73. Whether the "anti-human CD73 antibody" binds to human CD73 is confirmed by using a known binding activity measurement method. Examples of the binding activity measurement method include a method of Enzyme-Linked ImmunoSorbent Assay (ELISA) and the like. In a case of using the ELISA, for example, a human CD73 protein (for example, BPS Bioscience Inc., 71184) is immobilized on an ELISA plate and a test antibody is added thereto to be reacted. After the reaction, a secondary antibody such as an anti-IgG antibody, labeled with an enzyme such as horseradish peroxidase (HRP) or the like, is reacted. After the reaction, washing is performed, and then it is possible to confirm whether the test body binds to the human CD73 by identifying binding of the secondary antibody through activity measurement using a reagent detecting the activity (for example, in a case of HRP labeling, TMB+ substrate-chromogen (Dako Ltd.)). As a specific measurement method, the method described in Example 2 below can be used.

The anti-human CD73 antibody of the present invention includes, in addition to binding to human CD73, an antibody binding to CD73 derived from other animals (for example, monkey CD73), as long as the antibody binds to human CD73.

As a method for evaluating the activity of the anti-human CD73 antibody of the present invention, the enzyme inhibitory activity of human CD73 may be evaluated. As the methods for evaluating such activity, the methods described in Examples 3 and 4 below can be used, for example. The anti-human CD73 antibody of the present invention includes an antibody which binds to human CD73 and has an enzyme inhibitory activity of human CD73.

In addition, as a method for evaluating the activity of the anti-human CD73 antibody of the present invention, the activity of recovering AMP-dependently suppressed human T cell functions may be evaluated. As a method for evaluating such activity, it is possible to use the method as disclosed in Example 5 which will be described later. The anti-human CD73 antibody of the present invention includes an antibody which binds to human CD73 and has an activity of recovering AMP-dependently suppressed human T cell functions.

The anti-human CD73 antibody of the present invention can be easily prepared by a person skilled in the art using a known method in the field, based on sequence information on VH and VL of the present invention, which is disclosed in the present specification. The anti-human CD73 antibody of the present invention is not particularly limited, and can be produced according to the method described in the section of <Method for Producing the Anti-Human CD73 Antibody of the Present Invention or the Fused Form of the Present Invention, and the Anti-Human CD73 Antibody or the Fused Form thereof that can be Produced by the Method> described below.

The anti-human CD73 antibody of the present invention is further purified as needed, formulated according to a conventional method, and can be used for the prevention or the treatment of cancer. Cancers which are targets for the prevention or the treatment in the present invention are not particularly limited, but examples of the cancers include lung cancer, large intestine cancer, adrenocortical cancer, breast cancer, malignant melanoma, glioblastoma, ovarian cancer, medulloblastoma, bladder cancer, stomach cancer, pancreatic cancer, chronic myeloid leukemia, cutaneous T-cell lymphoma, glioblastoma, head and neck cancer, thyroid cancer, or prostate cancer.

<Fused Form and Modified Form of the Present Invention>

Any person skilled in the art can prepare a fused form in which the anti-human CD73 antibody or the antigen-binding fragment thereof of the present invention is fused with another peptide or protein, or also can prepare a modified form to which a modifying agent binds by using the anti-human CD73 antibody of the present invention. The fused form and the modified form of the present invention include a fused form in which the anti-human CD73 antibody or the antigen-binding fragment thereof of the present invention is fused with another peptide or protein or a modified form to which a modifying agent binds, as long as the fused form or the modified form binds to human CD73. Other peptides or proteins used for the fusion is not particularly limited, and examples thereof include human serum albumin, various tag peptides, artificial helix motif peptide, maltose-binding proteins, glutathione S transferase, various toxins, cytokine, chemokine, other peptides or proteins capable of promoting multimerization, and the like. The modifying agent used for the modification is not particularly limited, and examples thereof include polyethylene glycol, sugar chains, phospholipids, liposomes, low-molecular compounds, and the like. The fusion or modification may be direct fusion or modification, and may be fusion or modification via an arbitrary linker. The fused form of the present invention includes a fused form in which the anti-human CD73 antibody or the antigen-binding fragment thereof of the present invention is fused with a cytokine. The cytokine used in the fused form of the present invention is not limited to a cytokine present in nature, and may be a variant having the function. In one embodiment, a cytokine included in the fused form of the present invention is interleukin-7 (IL-7), interleukin 21 (IL-21), or a variant therefrom. In addition, a cytokine used in the fused form of the present invention may be a variant obtained by degrading a biological activity of IL-7 or IL-21.

In the fused form of the present invention, the heavy chain includes a heavy chain of an antibody comprised in the fused form and another peptide or protein with which the heavy chain is fused. In the fused from of the present invention, the light chain includes a light chain of an antibody comprised in the fused form and another peptide or protein with which the light chain is fused.

IL-7 is a cytokine which functions as a ligand with respect to an IL-7 receptor. It has been reported that IL-7 contributes to survival, proliferation, and differentiation of T cells, B cells, or the like (Curr Drug Targets., Vol. 7, p. 1571-1582, 2006). In the present invention, IL-7 includes IL-7 present in nature and a variant having the function. In one embodiment, IL-7 is human IL-7. In the present invention, human IL-7 includes human IL-7 present in nature and a variant having the function. In one embodiment, human IL-7 is selected from the group consisting of the following (1) to (3): (1) a polypeptide comprising the amino acid sequence shown by Accession No. NP_000871.1 and having the function of human IL-7, (2) a polypeptide consisting of the amino acid sequence in which 1 to 10 amino acids are deleted, substituted, inserted, and/or added and having the function of human IL-7, in the amino acid sequence shown by Accession No. NP_000871.1, and (3) a polypeptide comprising the amino acid sequence having equal to or greater than 90% identity to the amino acid sequence shown by Accession No. NP_000871.1 and having the function of human IL-7. In one embodiment, human IL-7 used in the present invention is a polypeptide consisting of the amino acid sequence shown by Accession No. NP_000871.1. Here, the function of human IL-7 is to perform actions for survival, proliferation, and differentiation of various human immune cells.

IL-21 is a cytokine which functions as a ligand with respect to an IL-21 receptor. It has been reported that IL-21 contributes to survival, proliferation, and differentiation of T cells, B cells, or the like (Cancer Lett., Vol. 358, p. 107-114, 2015). In the present invention, IL-21 includes IL-21 present in nature and a variant having the function. In one embodiment, IL-21 is human IL-21. In the present invention, human IL-21 includes human IL-21 present in nature and a variant having the function. In one embodiment, human IL-21 is selected from the group consisting of the following (1) to (3): (1) a polypeptide comprising the amino acid sequence shown by Accession No. NP_068575.1 and having the function of human IL-21, (2) a polypeptide consisting of the amino acid sequence in which 1 to 10 amino acids are deleted, substituted, inserted, and/or added and having the function of human IL-21, in the amino acid sequence shown by Accession No. NP_068575.1, and (3) a polypeptide comprising the amino acid sequence having equal to or greater than 90% identity to the amino acid sequence shown by Accession No. NP_068575.1 and having the function of human IL-21. In one embodiment, human IL-21 used in the present invention is a polypeptide consisting of the amino acid sequence shown by Accession No. NP_068575.1. Here, the function of human IL-21 is to perform actions for survival, proliferation, and differentiation of various human immune cells.

The fused form of the present invention also includes a fused form which is derived from posttranslational modification. Examples of posttranslational modification include various posttranslational modifications described in <Anti-Human CD73 Antibody of the Present Invention>.

In one embodiment, the fused form of the present invention is a fused form selected from the group consisting of the following (a) to (e):

(a) a fused form comprising a heavy chain consisting of the amino acid sequence shown by SEQ ID NO: 7 and a light chain consisting of the amino acid sequence shown by SEQ ID NO: 4;

(b) a fused form comprising a heavy chain consisting of the amino acid sequence shown by SEQ ID NO: 10 and a light chain consisting of the amino acid sequence shown by SEQ ID NO: 4;

(c) a fused form comprising a heavy chain consisting of the amino acid sequence shown by SEQ ID NO: 2 and a light chain consisting of the amino acid sequence shown by SEQ ID NO: 13;

(d) a fused form comprising a heavy chain consisting of the amino acid sequence shown by SEQ ID NO: 2 and a light chain consisting of the amino acid sequence shown by SEQ ID NO: 15; and (e) a fused form which is derived from posttranslational modification of the fused form of (a) to (d).

In one embodiment, the fused form of the present invention which is a fused form derived from posttranslational modification is the following fused form:

a fused form comprising a heavy chain consisting of the amino acid sequence of amino acid numbers 1 to 452 of SEQ ID NO: 2 and a light chain consisting of the amino acid sequence shown by SEQ ID NO: 13.

In one embodiment, the fused form of the present invention which is a fused form derived from posttranslational modification is the following fused form:

a fused form comprising a heavy chain consisting of the amino acid sequence of amino acid numbers 1 to 452 of SEQ ID NO: 2 and a light chain consisting of the amino acid sequence shown by SEQ ID NO: 15.

<Polynucleotide of the Present Invention>

The polynucleotide of the present invention includes a polynucleotide comprising a base sequence encoding VH of the anti-human CD73 antibody of the present invention and a polynucleotide comprising a base sequence encoding VL of the anti-human CD73 antibody of the present invention.

In one embodiment, the polynucleotide comprising a base sequence encoding VH of the anti-human CD73 antibody of the present invention is a polynucleotide comprising a base sequence encoding VH consisting of the amino acid sequence of amino acid numbers 1 to 123 of SEQ ID NO: 2.

Examples of the polynucleotide comprising a base sequence encoding VH consisting of the amino acid sequence of amino acid numbers 1 to 123 of SEQ ID NO: 2 include a polynucleotide comprising a base sequence of base sequence numbers 1 to 369 of SEQ ID NO: 1.

In one embodiment, the polynucleotide comprising a base sequence encoding VL of the anti-human CD73 antibody of the present invention is a polynucleotide comprising a base sequence encoding VL consisting of the amino acid sequence of amino acid numbers 1 to 109 of SEQ ID NO: 4.

Examples of the polynucleotide comprising a base sequence encoding VL consisting of the amino acid sequence of amino acid numbers 1 to 109 of SEQ ID NO: 4 include a polynucleotide comprising a base sequence of base sequence numbers 1 to 327 of SEQ ID NO: 3.

The polynucleotide of the present invention includes a polynucleotide comprising a base sequence encoding a heavy chain of the anti-human CD73 antibody of the present invention and a polynucleotide comprising a base sequence encoding a light chain of the anti-human CD73 antibody of the present invention.

In one embodiment, the polynucleotide comprising a base sequence encoding the heavy chain of the anti-human CD73 antibody of the present invention is a polynucleotide comprising a base sequence encoding the heavy chain consisting of the amino acid sequence shown by SEQ ID NO: 2.

Examples of the polynucleotide comprising a base sequence encoding the heavy chain consisting of the amino acid sequence shown by SEQ ID NO: 2 include a polynucleotide comprising a base sequence shown by SEQ ID NO: 1 or 11.

In one embodiment, the polynucleotide comprising a base sequence encoding the light chain of the anti-human CD73 antibody of the present invention is a polynucleotide comprising a base sequence encoding the light chain consisting of the amino acid sequence shown by SEQ ID NO: 4.

Examples of the polynucleotide comprising a base sequence encoding the light chain consisting of the amino acid sequence shown by SEQ ID NO: 4 include a polynucleotide comprising a base sequence shown by SEQ ID NO: 3 or 8.

The polynucleotide of the present invention includes a polynucleotide comprising a base sequence encoding a heavy chain of the fused form of the present invention and a polynucleotide comprising a base sequence encoding a light chain of the fused form of the present invention.

In one embodiment, the polynucleotide comprising a base sequence encoding the heavy chain of the fused form of the present invention is a polynucleotide comprising a base sequence encoding the heavy chain consisting of the amino acid sequence shown by SEQ ID NO: 7.

Examples of the polynucleotide comprising a base sequence encoding the heavy chain consisting of the amino acid sequence shown by SEQ ID NO: 7 include a polynucleotide comprising a base sequence shown by SEQ ID NO: 5 or 6.

In one embodiment, the polynucleotide comprising a base sequence encoding the light chain of the fused form of the present invention is a polynucleotide comprising a base sequence encoding the light chain consisting of the amino acid sequence shown by SEQ ID NO: 4.

Examples of the polynucleotide comprising a base sequence encoding the light chain consisting of the amino acid sequence shown by SEQ ID NO: 4 include a polynucleotide comprising a base sequence shown by SEQ ID NO: 3 or 8.

In one embodiment, the polynucleotide comprising a base sequence encoding the heavy chain of the fused form of the present invention is a polynucleotide comprising a base sequence encoding the heavy chain consisting of the amino acid sequence shown by SEQ ID NO: 10.

Examples of the polynucleotide comprising a base sequence encoding the heavy chain consisting of the amino acid sequence shown by SEQ ID NO: 10 include a polynucleotide comprising a base sequence shown by SEQ ID NO: 9 or 16.

In one embodiment, the polynucleotide comprising a base sequence encoding the heavy chain of the fused form of the present invention is a polynucleotide comprising a base sequence encoding the heavy chain consisting of the amino acid sequence shown by SEQ ID NO: 2.

Examples of the polynucleotide comprising a base sequence encoding the heavy chain consisting of the amino acid sequence shown by SEQ ID NO: 2 include a polynucleotide comprising a base sequence shown by SEQ ID NO: 1 or 11.

In one embodiment, the polynucleotide comprising a base sequence encoding the light chain of the fused form of the present invention is a polynucleotide comprising a base sequence encoding the light chain consisting of the amino acid sequence shown by SEQ ID NO: 13.

Examples of the polynucleotide comprising a base sequence encoding the light chain consisting of the amino acid sequence shown by SEQ ID NO: 13 include a polynucleotide comprising a base sequence shown by SEQ ID NO: 12.

In one embodiment, the polynucleotide comprising a base sequence encoding the light chain of the fused form of the present invention is a polynucleotide comprising a base sequence encoding the light chain consisting of the amino acid sequence shown by SEQ ID NO: 15.

Examples of the polynucleotide comprising a base sequence encoding the light chain consisting of the amino acid sequence shown by SEQ ID NO: 15 include a polynucleotide comprising a base sequence shown by SEQ ID NO: 14.

The polynucleotide of the present invention can be easily prepared by a person skilled in the art using a known method in the field based on the base sequence. For example, the polynucleotide of the present invention can be synthesized using a known gene synthesis method in the field. As the gene synthesis method, various methods such as a synthesis method of antibody genes described in WO90/07861 known by a person skilled in the art can be used.

<Expression Vector of the Present Invention>

An expression vector of the present invention includes an expression vector comprising a polynucleotide comprising a base sequence encoding VH of the anti-human CD73 antibody of the present invention, an expression vector comprising a polynucleotide comprising a base sequence encoding VL of the anti-human CD73 antibody of the present invention, and an expression vector comprising a polynucleotide comprising a base sequence encoding VH of the anti-human CD73 antibody of the present invention and a polynucleotide comprising a base sequence encoding VL of the antibody.

An expression vector of the present invention includes an expression vector comprising a polynucleotide comprising a base sequence encoding a heavy chain of the anti-human CD73 antibody of the present invention, an expression vector comprising a polynucleotide comprising a base sequence encoding a light chain of the anti-human CD73 antibody of the present invention, and an expression vector comprising a polynucleotide comprising a base sequence encoding the heavy chain of the anti-human CD73 antibody of the present invention and a polynucleotide comprising a base sequence encoding the light chain of the antibody.

An expression vector of the present invention includes an expression vector comprising a polynucleotide comprising a base sequence encoding a heavy chain of the fused form of the present invention, an expression vector comprising a polynucleotide comprising a base sequence encoding a light chain of the fused form of the present invention, and an expression vector comprising a polynucleotide comprising a base sequence encoding the heavy chain of the fused form and a polynucleotide comprising a base sequence encoding the light chain of the fused form.

The expression vectors used to express the polynucleotide of the present invention are not particularly limited as long as a polynucleotide comprising the base sequence encoding the heavy chain of the anti-human CD73 antibody or the fused form of the present invention and/or a polynucleotide comprising the base sequence encoding the light chain of the anti-human CD73 antibody or the fused form of the present invention can be expressed in various host cells of eukaryotic cells (for example, animal cells, insect cells, plant cells, and yeast) and/or prokaryotic cells (for example, *Escherichia coli*), and the polypeptides encoded by these can be produced. Examples of the expression vector include plasmid vectors, viral vectors (for example, adenovirus or retrovirus), and the like. In one embodiment, pEE6.4 or pEE12.4 (Lonza Biologics, Inc.) can be used as an expression vector.

The expression vector of the present invention may include a promoter that is operably linked to the polynucleotide of the present invention. Examples of the promoter for expressing the polynucleotide of the invention with animal cells include a virus-derived promoter such as CMV, RSV, or SV40, an actin promoter, an EF (elongation factor) 1α promoter, and a heat shock promoter. Examples of promoters for expressing the polynucleotide of the invention by bacteria (for example, *Escherichia*) include a trp promoter, a lac promoter, λPL promoter, and tac promoter. Further, examples of promoters for expressing the polynucleotide of the invention by yeast include a GAL1 promoter, a GAL10 promoter, a PHO5 promoter, a PGK promoter, a GAP promoter, and an ADH promoter.

In the case of using an animal cell, an insect cell, or yeast as the host cell, the expression vector of the present invention may include initiation codon and termination codon. In this case, the expression vector of the present invention may comprise an enhancer sequence, an untranslated region on the 5' side and the 3' side of genes encoding the antibody of the present invention or the heavy chain or the light chain, a secretory signal sequence, a splicing junction, a polyadenylation site, or a replicable unit. When *Escherichia coli* is used as the host cell, the expression vector of the present invention may comprise an initiation codon, a termination codon, a terminator region, and a replicable unit. In this case, the expression vector of the present invention may comprise a selection marker (for example, tetracycline resistant genes, ampicillin resistant genes, kanamycin resistant genes, neomycin resistant genes, or dihydrofolate reductase genes) which is generally used according to the purpose.

<Transformed Host Cell of the Present Invention>

The transformed host cell of the present invention includes a host cell transformed with the expression vector of the present invention, which is selected from the group consisting of the following (a) to (d):

(a) a host cell transformed with an expression vector comprising a polynucleotide comprising a base sequence encoding VH of the anti-human CD73 antibody of the present invention;

(b) a host cell transformed with an expression vector comprising a polynucleotide comprising a base sequence encoding VL of the anti-human CD73 antibody of the present invention;

(c) a host cell transformed with an expression vector comprising a polynucleotide comprising a base sequence encoding VH of the anti-human CD73 antibody of the present invention and a polynucleotide comprising a base sequence encoding VL of the antibody; and (d) a host cell transformed with an expression vector comprising a polynucleotide comprising a base sequence encoding VH of the anti-human CD73 antibody of the present invention and an expression vector comprising a polynucleotide comprising a base sequence encoding VL of the antibody.

The transformed host cell of the present invention includes a host cell transformed with the expression vector of the present invention, which is selected from the group consisting of the following (a) to (d):

(a) a host cell transformed with an expression vector comprising a polynucleotide comprising a base sequence encoding the heavy chain of the anti-human CD73 antibody of the present invention;

(b) a host cell transformed with an expression vector comprising a polynucleotide comprising a base sequence encoding the light chain of the anti-human CD73 antibody of the present invention;

(c) a host cell transformed with an expression vector comprising a polynucleotide comprising a base sequence encoding the heavy chain of the anti-human CD73 antibody of the present invention and a polynucleotide comprising a base sequence encoding the light chain of the anti-human CD73 antibody of the present invention; and (d) a host cell transformed with an expression vector comprising a polynucleotide comprising a base sequence encoding the heavy chain of the anti-human CD73 antibody of the present invention and an expression vector comprising a polynucleotide comprising a base sequence encoding the light chain of the antibody.

The transformed host cell of the present invention includes a host cell transformed with the expression vector of the present invention, which is selected from the group consisting of the following (a) to (d):

(a) a host cell transformed with an expression vector comprising a polynucleotide comprising a base sequence encoding the heavy chain of the fused form of the present invention;

(b) a host cell transformed with an expression vector comprising a polynucleotide comprising a base sequence encoding the light chain of the fused form of the present invention;

(c) a host cell transformed with an expression vector comprising a polynucleotide comprising a base sequence encoding the heavy chain of the fused form of the present invention and a polynucleotide comprising a base sequence encoding the light chain of the fused form; and (d) a host cell transformed with an expression vector comprising a polynucleotide comprising a base sequence encoding the heavy chain of the fused form of the present invention and an expression vector comprising a polynucleotide comprising a base sequence encoding the light chain of the fused form.

Examples of the transformed host cell of the present invention include a host cell transformed with an expression vector comprising a polynucleotide comprising a base sequence encoding the heavy chain of the anti-human CD73 antibody of the present invention and a polynucleotide comprising a base sequence encoding the light chain of the antibody, and a host cell transformed with an expression vector comprising a polynucleotide comprising a base sequence encoding the heavy chain of the anti-human CD73 antibody of the present invention and an expression vector comprising a polynucleotide comprising a base sequence encoding the light chain of the antibody.

The transformed host cell is not particularly limited as long as the host cell is appropriate for the expression vector being used, transformed with the expression vector, and can express the antibody or the fused form. Examples of the transformed host cell include various cells such as natural cells or artificially established cells which are generally used in the field of the present invention (for example, animal cells (for example, CHO-K1SV cells), insect cells (for example, Sf9), bacteria (for example, *Escherichia*), yeast (for example, *Saccharomyces* or *Pichia*) or the like). In one embodiment, cell lines such as CHO-K1SV cells, CHO-DG 44 cells, HEK293 cells, NS0 cells, or the like can be used as a transformed host cell.

A method of transforming the host cell is not particularly limited, and, for example, a calcium phosphate method or an electroporation method can be used.

<Method for Producing the Anti-Human CD73 Antibody of the Present Invention or the Fused Form of the Present Invention, and the Anti-Human CD73 Antibody or the Fused Form Thereof that can be Produced by the Method>

The method for producing the anti-human CD73 antibody of the present invention or the fused form of the present invention includes a method for producing an anti-human CD73 antibody, an antigen-binding fragment thereof, or a fused form of any one thereof by culturing host cell(s) selected from the group consisting of the following (a) to (c) to express the anti-human CD73 antibody, the antigen-binding fragment thereof, or the fused form of any one thereof:

(a) a host cell transformed with an expression vector comprising a polynucleotide comprising a base sequence encoding VH of the anti-human CD73 antibody of the present invention and a polynucleotide comprising a base sequence encoding VL of the antibody;

(b) a host cell transformed with an expression vector comprising a polynucleotide comprising a base sequence encoding VH of the anti-human CD73 antibody of the present invention and an expression vector comprising a polynucleotide comprising a base sequence encoding VL of the antibody; and (c) a host cell transformed with an expression vector comprising a polynucleotide comprising a base sequence encoding VH of the anti-human CD73 antibody of the present invention and a host cell transformed with an expression vector comprising a polynucleotide comprising a base sequence encoding VL of the antibody.

The method for producing the anti-human CD73 antibody of the present invention or the fused form of the present invention includes a method for producing an anti-human CD73 antibody or a fused form thereof by culturing host cell(s) selected from the group consisting of the following (a) to (c) to express the anti-human CD73 antibody or the fused from of thereof:

(a) a host cell transformed with an expression vector comprising a polynucleotide comprising a base sequence encoding the heavy chain of the anti-human CD73 antibody of the present invention and a polynucleotide comprising a base sequence encoding the light chain of the antibody;

(b) a host cell transformed with an expression vector comprising a polynucleotide comprising a base sequence encoding the heavy chain of the anti-human CD73 antibody of the present invention and an expression vector comprising a polynucleotide comprising a base sequence encoding the light chain of the antibody; and (c) a host cell transformed with an expression vector comprising a polynucleotide comprising a base sequence encoding the heavy chain of the anti-human CD73 antibody of the present invention and a host cell transformed with an expression vector comprising a polynucleotide comprising a base sequence encoding the light chain of the antibody.

The method for producing the fused form of the present invention includes a method for producing a fused form of the anti-human CD73 antibody by culturing host cell(s) selected from the group consisting of the following (a) to (c) to express the fused form of the anti-human CD73 antibody:

(a) a host cell transformed with an expression vector comprising a polynucleotide comprising a base sequence encoding the heavy chain of the fused form of the present invention and a polynucleotide comprising a base sequence encoding the light chain of the fused form;

(b) a host cell transformed with an expression vector comprising a polynucleotide comprising a base sequence encoding the heavy chain of the fused form of the present invention and an expression vector comprising a polynucleotide comprising a base sequence encoding the light chain of the fused form; and (c) a host cell transformed with an expression vector comprising a polynucleotide comprising a base sequence encoding the heavy chain of the fused form of the present invention and a host cell transformed with an expression vector comprising a polynucleotide comprising a base sequence encoding the light chain of the fused form.

The method for producing the anti-human CD73 antibody of the present invention or the fused form of the present invention is not particularly limited as long as it comprises a step of culturing the transformed host cells of the present invention to express the anti-human CD73 antibody, the antigen-binding fragment, or the fused from of any one thereof. Examples of the host cells used in the method include the transformed host cells of the present invention as described above.

The transformed host cell can be cultured by known methods. Culture conditions, for example, the temperature, pH of culture medium, and the culture time are appropriately selected. In a case where the host cell is an animal cell, examples of the culture medium include MEM culture medium supplemented with approximately 5% to 20% of fetal bovine serum (Science, Vol. 130, p. 432-437, 1959), DMEM culture medium (Virology, Vol. 8, p. 396, 1959), RPMI1640 culture medium (J. Am. Med. Assoc., Vol. 199, p. 519, 1967), and a 199 culture medium (Exp. Biol. Med., Vol. 73, p. 1-8, 1950). The pH of the culture medium is preferably approximately 6 to 8, and the culture is generally carried out at approximately 30° C. to 40° C. for approximately 15 hours to 336 hours while air ventilating and stirring if necessary. In a case where the host cell is an insect cell, as the culture medium, for example, Grace's culture medium (Proc Natl Acad Sci USA., Vol. 82, p. 8404, 1985) supplemented with fetal bovine serum can be used. The pH of the culture medium is approximately 5 to 8, for example, and the culture is generally carried out at approximately 20° C. to 40° C. for approximately 15 hours to 100 hours while air ventilating and stirring if necessary. In a case where the host cell is *Escherichia coli* or yeast, as the culture medium, for example, liquid culture medium supplemented with a source of nutrients is appropriate. The nutrient culture medium includes a carbon source, an inorganic nitrogen source, or an organic nitrogen source necessary for the growth of the transformed host cell. Examples of the carbon source include glucose, dextran, soluble starch, and sucrose and examples of the inorganic nitrogen source or the organic nitrogen source include ammonium salts, nitrate salts, amino acids, corn steep liquor, peptone, casein, meat extract, soybean meal, and potato extract. Other nutrients (for example, inorganic salts (for example, calcium chloride, sodium dihydrogen phosphate, and magnesium chloride), vitamins), and antibiotics (for example, tetracycline, neomycin, ampicillin, and kanamycin) may be included as desired. The pH of the culture medium is approximately 5 to 8, for example. In a case where the host cell is *Escherichia coli*, examples of the culture medium include LB culture medium and M9 culture medium (Molecular. Cloning, Cold Spring Harbor Laboratory, Vol. 3, A2.2). The culture is generally carried out at approximately 14° C. to 43° C. for approximately 3 hours to 24 hours while air ventilating and stirring if necessary. In a case where the host cell is yeast, as the culture medium, for example, Burkholder minimal medium (Proc Natl Acad Sci USA., Vol. 77, p. 4505, 1980) can be used. The culture is generally carried out at approximately 20° C. to 35° C. for approximately 14 hours to 144 hours while air ventilating and stirring if necessary. By carrying out the culture in the above-described manner, it is possible to express the anti-human CD73 antibody of the present invention.

The method for producing the anti-human CD73 antibody of the present invention or the fused form of the present invention may further include recovering, isolating, or purifying the anti-human CD73 antibody, the antigen-binding fragment thereof, or the fused form of any one thereof, in addition to culturing the transformed host cell of the present invention to express the anti-human CD73 antibody, the antigen-binding fragment thereof, or the fused form of any one thereof. Examples of the isolation or purification method include methods using solubility such as salting-out and the solvent precipitation method, methods using the difference in molecular weight such as dialysis, ultrafiltration, and gel filtration, methods using an electric charge such as ion exchange chromatography and hydroxylapatite chromatography, methods using specific affinity such as affinity chromatography, methods using the difference in hydrophobicity such as reverse phase high performance liquid chromatography, and methods using the difference in the isoelectric point such as isoelectric focusing phoresis. In one embodiment, the antibody accumulated in a culture supernatant can be purified by various chromatographies, for example, column chromatography using Protein A column or Protein G column.

The anti-human CD73 antibody of the present invention or the fused form of the present invention also includes an anti-human CD73 antibody and an antigen-binding fragment thereof, or a fused form of any one thereof produced by the method for producing the anti-human CD73 antibody of the present invention or the fused form of the present invention.

<Pharmaceutical Composition of the Present Invention>

The pharmaceutical composition of the present invention includes a pharmaceutical composition comprising the anti-human CD73 antibody of the present invention, the antigen-binding fragment thereof, or the fused form of the present invention, and pharmaceutically acceptable excipients. The pharmaceutical composition of the present invention can be prepared by a method being generally used with excipients, that is, excipients for medicine or carriers for medicine being generally used in the field. Examples of dosage forms of the pharmaceutical compositions include parenteral drug such as an injection drug and a drip infusion drug, and these can be administered by intravenous administration, subcutaneous administration, or the like. In drug preparation, excipients, carriers, and additives in accordance with the dosage forms can be used within the pharmaceutically acceptable range.

The pharmaceutical composition of the present invention may include plural kinds of anti-human CD73 antibody of the present invention. For example, the present invention also includes a pharmaceutical composition containing an antibody or an antigen-binding fragment thereof which does not undergo deletion of lysine at the C terminal and pyroglutamylation at the N terminal and/or an antibody or an antigen-binding fragment thereof which have undergone deletion of lysine at the C terminal and/or pyroglutamylation at the N terminal.

The pharmaceutical composition of the present invention may include plural kinds of fused form of the present invention. For example, the pharmaceutical composition of the present invention also includes a pharmaceutical composition containing a fused form which does not undergo deletion of lysine at the C terminal and pyroglutamylation at the N terminal and/or a fused form which has undergone deletion of lysine at the C terminal and/or pyroglutamylation at the N terminal.

In one embodiment, the pharmaceutical composition of the present invention contains an anti-human CD73 antibody or an antigen-binding fragment thereof comprising a heavy chain variable region consisting of the amino acid sequence of amino acid numbers 1 to 123 of SEQ ID NO: 2 and a light chain variable region consisting of the amino acid sequence of amino acid numbers 1 to 109 of SEQ ID NO: 4, and an anti-human CD73 antibody or an antigen-binding fragment thereof which is derived from posttranslational modification of the anti-human CD73 antibody or the antigen-binding fragment thereof.

The pharmaceutical composition of the present invention also includes a pharmaceutical composition containing an antibody in which lysine at the C terminal of the heavy chain is deleted, an antibody or an antigen-binding fragment thereof which has undergone pyroglutamylation at the N terminal, an antibody in which lysine at the C terminal of the heavy chain is deleted and which has undergone pyroglutamylation at the N terminal, and/or an antibody or an antigen-binding fragment thereof which has lysine at the C terminal of the heavy chain and does not undergo pyroglutamylation at the N terminal.

In one embodiment, the pharmaceutical composition of the present invention is a pharmaceutical composition comprising an anti-human CD73 antibody comprising a heavy chain consisting of the amino acid sequence shown by SEQ ID NO: 2 and a light chain consisting of the amino acid sequence shown by SEQ ID NO: 4, an anti-human CD73 antibody comprising a polynucleotide consisting of the amino acid sequence of an antibody derived from posttranslational modification of the anti-human CD73 antibody, and a pharmaceutically acceptable excipient.

In one embodiment, the pharmaceutical composition of the present invention is a pharmaceutical composition comprising a fused form of an anti-human CD73 antibody comprising the heavy chain consisting of the amino acid sequence shown by SEQ ID NO: 7 and the light chain consisting of the amino acid sequence shown by SEQ ID NO: 4, a fused form comprising a polypeptide consisting of the amino acid sequence of a fused form derived from posttranslational modification of the fused form, and a pharmaceutically acceptable excipient.

In one embodiment, the pharmaceutical composition of the present invention is a pharmaceutical composition comprising a fused form of an anti-human CD73 antibody comprising a heavy chain consisting of the amino acid sequence shown by SEQ ID NO: 10 and a light chain consisting of the amino acid sequence shown by SEQ ID NO: 4, a fused form comprising a polypeptide consisting of the amino acid sequence of a fused form derived from posttranslational modification of the fused form, and a pharmaceutically acceptable excipient.

In one embodiment, the pharmaceutical composition of the present invention is a pharmaceutical composition comprising a fused form of an anti-human CD73 antibody comprising a heavy chain consisting of the amino acid sequence shown by SEQ ID NO: 2 and a light chain consisting of the amino acid sequence shown by SEQ ID NO: 13, a fused form comprising a polypeptide consisting of the amino acid sequence of a fused form derived from posttranslational modification of the fused form, and a pharmaceutically acceptable excipient.

In one embodiment, the pharmaceutical composition of the present invention is a pharmaceutical composition comprising a fused form of an anti-human CD73 antibody comprising a heavy chain consisting of the amino acid sequence shown by SEQ ID NO: 2 and a light chain consisting of the amino acid sequence shown by SEQ ID NO: 15, a fused form comprising a polypeptide consisting of the amino acid sequence of a fused form derived from posttranslational modification of the fused form, and a pharmaceutically acceptable excipient.

The addition amount of the anti-human CD73 antibody, the fused form, and the modified form of the present invention in formulation varies depending on the degree of a patient's symptoms, the age of a patient, a dosage form of the drug to be used, the binding titer of the antibody, or the like, and for example, an addition amount of approximately 0.001 mg/kg to 100 mg/kg can be used.

The pharmaceutical composition of the present invention can be used as an agent for treating cancer.

The pharmaceutical composition of the present invention includes a pharmaceutical composition for preventing or treating cancer comprising the anti-human CD73 antibody, the fused form, or the modified form of the present invention. Further, the present invention includes a method for treating or preventing cancer comprising administering a therapeutically effective amount of the anti-human CD73 antibody, the fused form, or the modified form of the present invention. Further, the present invention includes the anti-human CD73 antibody, the fused form, and the modified form of the present invention for use in preventing or treating cancer. In addition, the present invention includes use of the anti-human CD73 antibody, the fused form, and the modified form of the present invention for the manufacture of a pharmaceutical composition for preventing or treating cancer. Cancers which are targets for the prevention or the treatment in the present invention are not particularly limited, but examples of the cancers include lung cancer, large intestine cancer, adrenocortical cancer, breast cancer, malignant melanoma, glioblastoma, ovarian cancer, medulloblastoma, bladder cancer, stomach cancer, pancreatic cancer, chronic myeloid leukemia, cutaneous T-cell lymphoma, glioblastoma, head and neck cancer, thyroid cancer, or prostate cancer.

For better understanding regarding the present invention, specific examples referred to will be provided, but these are merely examples and the present invention is not limited thereto.

EXAMPLES

Unless otherwise noted, the tests are performed according to the known methods. In addition, with regard to parts using commercially available reagents or kits, the tests are performed according to the instructions of the commercially available products.

Example 1: Preparation of Anti-Human CD73 Antibody

An anti-human CD73 antibody was prepared using a human monoclonal antibody developing technology "VelocImmune" (VelocImmune antibody technology; Regeneron Pharmaceuticals, Inc. (U.S. Pat. No. 6,596,541)) mouse. The antibody acquired by the technology is a chimeric antibody of which the variable region is derived from a human and the constant region is derived from a mouse. A VelocImmune mouse was immunized with an adjuvant for causing an immune reaction together with a human CD73 protein. The human CD73 protein was manufactured by the following technique. A base sequence encoding a HisTag sequence (His×6) and a termination codon was added to the 3' terminal of a base sequence of base numbers 1 to 1641 of a human CD73 gene (ORIGENE Technologies, Inc., RC209568) by a gene engineering technique using a gene introduced with a vector for mammalian cell expression as an expression vector. The expression vector was transfected to an Expi293F™ cell (Thermo Fisher Scientific Inc.) and a fusion protein of human CD73 and HisTag (human CD73-His protein) was purified from recovered supernatant. The purified human CD73-His protein was immunized into the mouse several times, and then hybridoma was prepared according to the conventional method. Using the antibody purified with hybridoma supernatant, a hybridoma clone producing an antibody having a function of inhibiting human CD73 enzymatic activity was selected. Then, genes encoding a heavy chain and a light chain of an antibody from hybridoma were cloned. As for the gene cloning, according to the conventional method, antibody gene sequences of cDNA prepared by extracted RNA of hybridoma were analyzed and sequence determination was performed. In addition, the amino acid sequence was analyzed, and Kabat et al. database (Kabat et al. Sequences of Proteins of Immunological Interest, Fifth Edition, NIH Publication No. 91-3242, 1991) was referred to so as to determine CDR sequence and FR sequence. In order to improve physical properties and stability, FR of the heavy chain and the light chain of some clones was substituted with FR of the heavy chain and the light chain of other human antibodies, respectively. The VH and the VL of the substituted antibody sequence were respectively linked to a human Igγ1 constant region (in some clones, human Igγ1 constant region having amino acid mutations of L234A, L235A and P331S) and human Igκ1 constant region by the PCR method, inserted into a GS vector (Lonza Biologics, Inc.) which is a vector for mammalian cell expression, thereby constructing an expression vector. Specifically, genes encoding signal sequences (Protein Eng., Vol. 1, p. 499-505, 1987) and human Igγ1 constant region genes were respectively ligated to the 5' side and the 3' side of the heavy chain variable region genes of the antibody, and then the heavy chain genes were inserted into a GS vector pEE6.4. Further, genes encoding signal sequences (Protein Eng., Vol. 1, p. 499-505, 1987) and the constant region genes of a human κ chain were respectively ligated to the 5' side and the 3' side of the light chain variable region genes, and then the light chain genes were inserted into a GS vector pEE12.4.

Using an expression vector comprising the antibody heavy chain and the antibody light chain thereof, a purified antibody was acquired from a transient expression or stable expression line. With regard to the transient expression, specifically, both expression vectors of the above-described antibody heavy chain and antibody light chain were transfected to CHOKISV cells (Lonza Biologics, Inc.) using MaxCyte STX (trade name) (MaxCyte Inc.), and cultured for about 7 days. The culture supernatants of the transient expression or stable expression were purified using MabSelect SuRe (GE Healthcare Japan Corporation), Vivapure (trade name) Q Maxi H (Sartorius Group), and the like, thereby obtaining purified antibodies.

As a result of selecting clones having the function of inhibiting human CD73 enzymatic activity from a number of purified antibodies, it was evident that an anti-human CD73 antibody named CDS-1 has the strongest function of inhibiting enzymatic activity.

The base sequence encoding residue number 1 of a variable region to the C terminal of a constant region according to Kabat numbering, of the heavy chain of CDS-1 is shown by SEQ ID NO: 1, the amino acid sequence encoded by the base sequence is shown by SEQ ID NO: 2, the base sequence encoding residue number 1 of a variable region to the C terminal of a constant region according to Kabat numbering, of the light chain of the antibody is shown by SEQ ID NO: 3, and the amino acid sequence encoded by the base sequence is shown by SEQ ID NO: 4.

The VH of CDS-1 consists of the amino acid sequence of the amino acid numbers 1 to 123 of SEQ ID NO: 2, CDR1, CDR2, and CDR3 of the heavy chain respectively consist of the amino acid sequences of amino acid numbers 31 to 35, 50 to 66, and 99 to 112 of SEQ ID NO: 2. The VL of the antibody consists of the amino acid sequence of the amino acid numbers 1 to 109 of SEQ ID NO: 4, and CDR1, CDR2, and CDR3 of the light chain respectively consist of the amino acid sequences of amino acid numbers 24 to 34, 50 to 56, and 89 to 98 of SEQ ID NO: 4.

A fused form in which human IL-7 is fused to the C terminal side of the heavy chain of CDS-1 was acquired and named CDS-3. The base sequence encoding the residue number 1 of a variable region to the C terminal of a constant region according to Kabat numbering, and human IL-7 via a linker, of the heavy chain of CDS-3 is shown by SEQ ID NOS: 5 and 6, the amino acid sequence encoded by the base sequence is shown by SEQ ID NO: 7, the base sequence encoding the residue number 1 of a variable region to the C terminal of a constant region according to Kabat numbering, of the light chain of the fused form is shown by SEQ ID NOS: 3 and 8, the amino acid sequence encoded by the base sequence is shown by SEQ ID NO: 4, and the heavy chain of CDS-3 consists of the amino acid sequences in which the amino acid sequence of human IL-7 consisting of the amino acid sequence of amino acid numbers 464 to 615 of SEQ ID NO: 7 is fused to the C terminal side of the heavy chain of CDS-1 via a linker consisting of the amino acid sequence of amino acid numbers 454 to 463 of SEQ ID NO: 7.

A fused form in which human IL-7 variant is fused to the C terminal side of the heavy chain of CDS-1 was acquired and named CDS-6. The base sequence encoding the residue number 1 of a variable region to the C terminal of a constant region according to Kabat numbering, and human IL-7 variant via a linker, of the heavy chain of CDS-6 is shown by SEQ ID NOS: 9 and 16, the amino acid sequence encoded by the base sequence is shown by SEQ ID NO: 10, the base sequence encoding the residue number 1 of a variable region to the C terminal of a constant region according to Kabat numbering, of the light chain of the fused form is shown by SEQ ID NOS: 3 and 8, and the amino acid sequence encoded by the base sequence is shown by SEQ ID NO: 4, respectively. The heavy chain of CDS-6 consists of the amino acid sequences in which the amino acid sequence of human IL-7 variant consisting of the amino acid sequence of amino acid numbers 464 to 615 of SEQ ID NO: 10 is fused to the C terminal side of the heavy chain of CDS-1 via a linker consisting of the amino acid sequence of amino acid numbers 454 to 463 of SEQ ID NO: 10.

A fused form in which human IL-21 is fused to the C terminal side of the light chain of CDS-1 was acquired and named CDS-7. The base sequence encoding the residue number 1 of a variable region to the C terminal of a constant region according to Kabat numbering, of the heavy chain of CDS-7 is shown by SEQ ID NO: 11, the amino acid sequence encoded by the base sequence is shown by SEQ ID NO: 2, the base sequence encoding the residue number 1 of a variable region to the C terminal of a constant region according to Kabat numbering and IL-21 via a linker, of the light chain of the fused form is shown by SEQ ID NO: 12, and the amino acid sequence encoded by the base sequence is shown by SEQ ID NO: 13. The light chain of CDS-7 consists of the amino acid sequences in which the amino acid sequence of human IL-21 consisting of the amino acid sequence of amino acid numbers 226 to 358 of SEQ ID NO: 13 is fused to the C terminal side of the light chain of CDS-1 via a linker consisting of the amino acid sequence of amino acid numbers 216 to 225 of SEQ ID NO: 13.

A fused form in which human IL-21 variant is fused to the C terminal side of the light chain of CDS-1 was acquired and named CDS-8. The base sequence encoding the residue number 1 of a variable region to the C terminal of a constant region according to Kabat numbering, of the heavy chain of CDS-8 is shown by SEQ ID NO: 11, the amino acid sequence encoded by the base sequence is shown by SEQ ID NO: 2, the base sequence encoding the residue number 1 of a variable region to the C terminal of a constant region according to Kabat numbering and IL-21 variant via a linker, of the light chain of the fused form is shown by SEQ ID NO: 14, and the amino acid sequence encoded by the base sequence is shown by SEQ ID NO: 15. The light chain of CDS-8 consists of the amino acid sequences in which the amino acid sequence of human IL-21 variant consisting of the amino acid sequence of amino acid numbers 226 to 358 of SEQ ID NO: 15 is fused to the C terminal side of the light chain of CDS-1 via a linker consisting of the amino acid sequence of amino acid numbers 216 to 225 of SEQ ID NO: 15.

Purified CDS-3, CDS-6, CDS-7 and CDS-8 were acquired according to the above-described method.

Based on information illustrated in FIG. 1C and FIG. 1D of Patent Document 1, an expression vector expressing an antibody named MEDI9447 was prepared. Based on information shown by SEQ ID NOS: 21 and 22 of Patent Document 2, an expression vector expressing an antibody named 6E1 was prepared. Based on information shown by SEQ ID NOS: 133 and 102 of Patent Document 3, an expression vector expressing an antibody named CD73.4IgG2CS-IgG1.1f was prepared. Genes encoding signal sequences were inserted into these expression vectors according to the conventional method.

Purified MEDI9447, CD73.4IgG2CS-IgG1.1f, and 6E1 were acquired according to the conventional method and used for comparison.

As a result of analyzing amino acid modification of the purified CDS-1, CDS-7, and CDS-8, deletion of lysine at the C terminal of the heavy chain occurred in most purified antibodies.

As a result of analyzing amino acid modification of the purified CDS-3, the heavy chain was a sequence corresponding to SEQ ID NO: 7 and the light chain was a sequence corresponding to SEQ ID NO: 4.

As a result of analyzing amino acid modification of the purified CDS-6, the light chain was a sequence corresponding to SEQ ID NO: 4. Since sugar chains in the heavy chain were not completely cut, the type of amino acid modification cannot be specified.

Example 2: Evaluation of Binding Activity of Anti-Human CD73 Antibody to Human CD73 Protein In order to evaluate the binding activity of CDS-1, CDS-3, CDS-6, CDS-7, and CDS-8 acquired in Example 1 to human CD73, the ELISA was performed using a human CD73 protein. The human CD73 protein (BPS Bioscience Inc., 71184) diluted in PBS (Life Technologies, Inc.) to have a concentration of 4 µg/mL was added to a MaxiSorp 384-well plate Clear (Thermo Fisher Scientific Inc.) by an amount of 20 µL/well, and then immobilized overnight at a temperature of 4° C. The next day, the resultant was washed with a wash solution (0.05% Tween-20 containing Tris-buffered saline (TBS)) once, Blocking One (Nacalai tesque, Inc.) was added thereto in an amount of 100 µL/well, and the resultant was blocked at room temperature for 30 minutes. The resultant was washed with the wash solution once again, and the purified CDS-1, the purified CDS-3, the purified CDS-6, the purified CDS-7, or the purified CDS-8 prepared in Example 1 was added thereto by an amount of 20 µL/well, respectively. These purified antibodies were diluted using a reaction buffer obtained by mixing the same amount of PBS and Blocking One, and dilution was performed in 12 steps from 10 µg/mL to 56 pg/mL. The resultant was reacted at room temperature for 1 hour, and then washed three times with a wash solution. 20 µL/well of a human IgG-heavy and light chain cross-adsorbed antibody (Bethyl Laboratories Inc., A80-219P) which had been diluted 4000-fold with a reaction buffer was added thereto, and the resultant was reacted at room temperature for 1 hour. The resultant was washed with a wash solution three times, and 20 µL/well of TMB+substrate-chromogen (DAKO Ltd., 51599) was added thereto. After 5 minutes, 20 µL/well of 1M sulfuric acid (Wako Pure Chemical Industries, Ltd.) was added thereto and the reaction was stopped. The values of absorbance at 450 nm and 540 nm were measured by Infinite M200 PRO (TECAN Inc.), and $EC_{50}$ values of CDS-1, CDS-3, CDS-6, CDS-7, and CDS-8 with respect to the human CD73 protein were calculated. In calculation of the $EC_{50}$ values, the ordinate represents a difference in the measurement values of absorbance at 450 nm and 540 nm, and the abscissa represents an antibody concentration value. In addition, a measurement value when the measurement value can be determined to reach a convergence value according to the increase in the antibody concentration, from the shape of the sigmoid curve drawn on the graph, was set to 100%, and a measurement value when the measurement value can be determined to reach a convergence value according to the decrease in the antibody concentration therefrom was set to 0%. This assay was independently performed, and the $EC_{50}$ values were calculated from the 4-parameter logistic curve regression (Table 1).

TABLE 1

| | $EC_{50}$ (ng/mL) | |
|---|---|---|
| | First | Second |
| CDS-1 | 3.9 | 8.8 |
| CDS-3 | Not performed | 20.9 |
| CDS-6 | Not performed | 19.6 |
| CDS-7 | Not performed | 20.1 |
| CDS-8 | Not performed | 23.9 |

As a result, it was evident that CDS-1, CDS-3, CDS-6, CDS-7, and CDS-8 bind to the human CD73 protein.

Example 3: Evaluation of Enzyme Inhibitory Activity of Anti-Human CD73 Antibody to Human CD73 Protein In order to evaluate inhibition of CDS-1, CDS-3, CDS-6, CDS-7, and CDS-8 acquired in Example 1 against enzymatic activity of human CD73, an enzyme assay was performed using a human CD73 protein. In this example, MEDI9447, CD73.4IgG2CS-IgG1.1f, and 6E1 were used for comparison. 25 mM Tris-buffered saline containing 5 mM magnesium chloride was manufactured with hydrochloric acid to have a pH of 7.5, and set as an assay buffer. A human CD73 protein (R&D Systems, Inc., 5795) prepared with an assay buffer such that the final concentration was adjusted to 15 ng/mL, a purified CDS-1, a purified CDS-3, a purified CDS-6, a purified CDS-7, a purified CDS-8, a purified MEDI9447, a purified CD73.4IgG2CS-IgG1.1f, or a purified 6E1 diluted in an assay buffer was added to a 96-well assay plate Clear (Corning, Inc.) by an amount of 20 μL/well, respectively, and the resultant was reacted at room temperature for 30 minutes. These purified antibodies were diluted using an assay buffer, and the dilution was performed in 11 steps such that the final concentration was adjusted to 20 μg/mL to 0.339 ng/mL. AMP (SIGMA-ALDRICH Corporation, A1752-1G) diluted in an assay buffer was added by an amount of 20 μL/well such that the final concentration was adjusted to 30 μM thereto, and the resultant was reacted at room temperature for 45 minutes. 60 μL/well of acetonitrile was added thereto to stop the reaction, and the adenosine concentration was measured by LC/MS (LC: Shimadzu Corporation SIL-HTc or Waters Corporation Acquity UPLC I-Class, Column: Agilent Technologies, Inc. ZORBAX SB-Aq 1.8 μm 2.1×30 mm, MS: AB Sciex Ltd. API4000). On the basis of the measured adenosine concentration, inhibition of CDS-1 and the like against enzymatic activity of human CD73 was evaluated based on the measured $EC_{50}$ values. In calculation of the $EC_{50}$ values, the ordinate represents a measured adenosine concentration value, and the abscissa represents an antibody concentration value. In addition, an adenosine concentration value when the adenosine concentration value can be determined to reach a convergence value according to the increase in the antibody concentration, from the shape of the sigmoid curve drawn on the graph, was set to 100%, and an adenosine concentration value when the adenosine concentration value can be determined to reach a convergence value according to the decrease in the antibody concentration therefrom was set to 0%. This assay was independently performed, and the $EC_{50}$ values were calculated from the 4-parameter logistic curve regression (Table 2). As reported in Non-Patent Document 1, MEDI9447 was characterized to have a property of showing bell-shaped inhibition (FIG. 1). In addition, the convergence value of CD73.4IgG2CS-IgG1.1f was higher than the convergence value of the adenosine concentration value according to the increase in the antibody concentration of CDS-1.

TABLE 2

| | $EC_{50}$ (ng/mL) | |
|---|---|---|
| | Frist | Second |
| CDS-1 | 16.8 | 9.2 |
| CDS-3 | Not performed | 19.4 |
| CDS-6 | Not performed | 20.4 |
| CDS-7 | Not performed | 17.5 |
| CDS-8 | Not performed | 21.1 |

As a result, it was evident that CDS-1, CDS-3, CDS-6, CDS-7, and CDS-8 inhibit enzymatic activity of human CD73 proteins.

Example 4: Evaluation of Enzyme Inhibitory Activity of Anti-Human CD73 Antibody in Human CD73 Expression Cells In order to evaluate inhibition of CDS-1, CDS-3, CDS-6, CDS-7, and CDS-8 acquired in Example 1 against the enzymatic activity of human CD73, an enzyme assay was performed using a cancer cell line NCI-H1373 (ATCC: CRL-5866) endogenously expressing human CD73. NCI-H1373 cells were suspended in PBS (Life Technologies, Inc.), and added to a 96-well V-bottom plate (Sumitomo Bakelite Co., Ltd.) by an amount of 30 μL/well such that the final cell concentration was adjusted to $4 \times 10^4$ cells/well. Immediately thereafter, a purified CDS-1, a purified CDS-3, a purified CDS-6, a purified CDS-7, or a purified CDS-8 was respectively added by an amount of 10 μL/well. These purified antibodies were diluted using PBS, and the dilution was performed in 11 steps such that the final concentration was adjusted to 50.0 μg/mL to 0.847 ng/mL. After being reacted at room temperature for 30 minutes, AMP (SIGMA-ALDRICH Corporation, A1752-1G) was added by an amount of 10 μL/well such that the final concentration was adjusted to 180 μM. After being reacted at room temperature for 30 minutes, the plate was centrifuged at a temperature of 4° C. at 340×g. 15 μL/well of supernatant was transferred from the centrifuged plate to the newly prepared 96-well V-bottom plate (Sumitomo Bakelite Co., Ltd.) by, and 15 μL/well of acetonitrile was added thereto. The adenosine concentration was measured by LC/MS (described in Example 3), and the inhibition of CDS-1, CDS-3, CDS-6, CDS-7, and CDS-8 against the enzymatic activity of human CD73 based on the measured $EC_{50}$ values. This assay was independently performed, and the $EC_{50}$ values were calculated by the measurement method described in Example 3 (Table 3).

TABLE 3

|  | $EC_{50}$ (ng/mL) | |
| --- | --- | --- |
|  | First | Second |
| CDS-1 | 785 | 579 |
| CDS-3 | Not performed | 455 |
| CDS-6 | Not performed | 678 |
| CDS-7 | Not performed | 712 |
| CDS-8 | Not performed | 750 |

As a result, it was evident that CDS-1, CDS-3, CDS-6, CDS-7, and CDS-8 inhibit enzymatic activity of human CD73 in NCI-H1373 cells.

Figure 2:
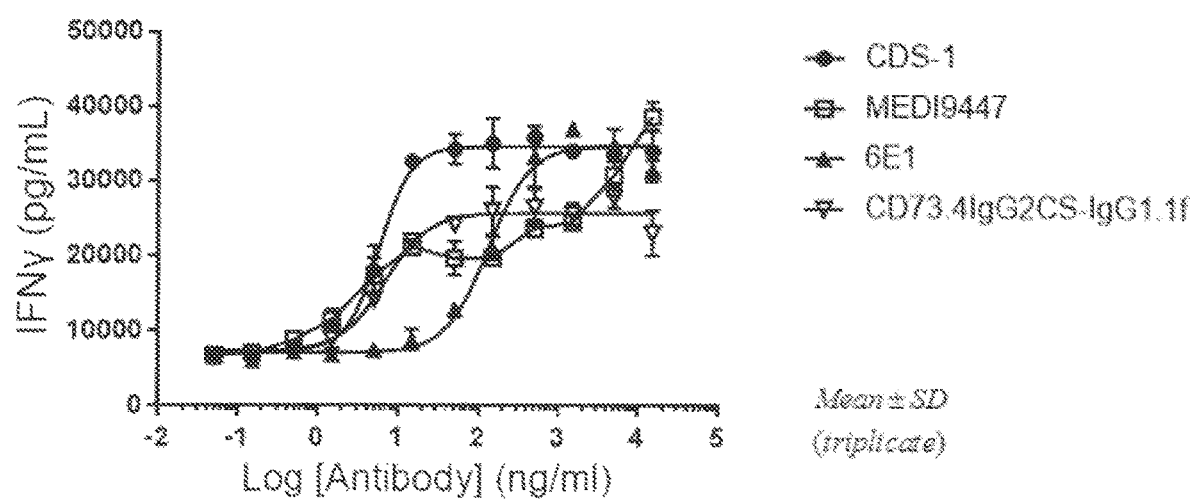
FIG. 2 is a view illustrating recovery of human T cell functions due to CDS-1, MEDI9447, 6E1, and CD73.4IgG2CS-IgG1.1f, using a production amount of IFNγ from human T cells as an index.
Figure 3:
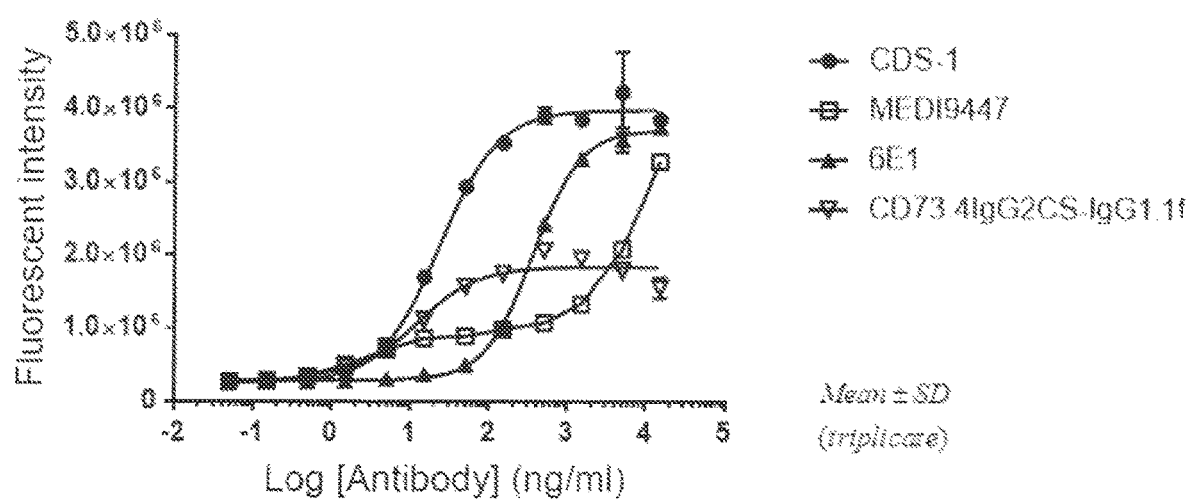
FIG. 3 is a view illustrating recovery of human T cell functions due to CDS-1, MEDI9447, 6E1, and CD73.4IgG2CS-IgG1.1f, using proliferation of human T cells as an index.

Example 5: Evaluation of Effect of Anti-Human CD73 Antibody on Recovery of AMP-Dependently Suppressed Human T Cell Functions In order to evaluate the effect of CDS-1 acquired in Example 1 on recovery of AMP-dependently suppressed human T cell functions, an assay was performed using a human T cell expressing human CD73. In this assay, it is possible to evaluate an antibody which activates anti-tumor immunity by recovering functions of immune cells suppressed by AMP using recovery of human T cell functions as an index. In this example, MEDI9447, CD73.4IgG2CS-IgG1.1f, and 6E1 were used for comparison. A human T cell was isolated from a human peripheral blood mononuclear cell (AllCells, LLC) using Pan T Cell Isolation Kit (Miltenyi Biotec Ltd., 130-096-535), suspended on a TexMACS™ culture medium (Miltenyi Biotec Ltd., 130-097-196), and added to a 96-well flat bottom plate (AGC TECHNO GLASS Co., Ltd.) by an amount of 50 µL/well such that the final cell density was adjusted to $1\times10^5$ cells/well. Immediately thereafter, a purified CDS-1, a purified MEDI9447, a purified 6E1, or a purified CD73.4IgG2CS-IgG1.1f was respectively added thereto by an amount of 25 µL/well. These purified antibodies were diluted using the TexMACS™ culture medium, and the dilution was performed in 12 steps such that the final concentration was adjusted to 15 µg/mL to 0.05 ng/mL. Further, AMP (SIGMA-ALDRICH Corporation) was added by an amount of 50 µL/well such that the final concentration was adjusted to 250 µM. Immediately thereafter, Dynabeads Human T-Activator CD3/CD28 (Thermo Fisher Scientific Inc., 11131D) was added thereto by an amount of 50 µL/well such that the final concentration was adjusted to $1\times10^5$ dynabeads/well. Then, a TexMACS™ culture medium was added such that a reaction solution of each well was 200 µL, and cultured in a 5% $CO_2$ incubator at a temperature of 37° C. for 3 days. 100 µL of cultured supernatant after 3 days was collected, and the interferon gamma (IFNγ) concentration in the supernatant was measured based on the protocol of AlphaLISA (trade name) IFNγ Immunoassay Kit (PerkinElmer Inc., AL217C). In addition, in order to analyze proliferation of human T cells, 20 µL/well of CellTiter-Blue Reagent was added to the above-described plate from which 100 µL of supernatant had been removed, based on the protocol of CellTiter-Blue (trade name) Cell Viability Assay (Promega K.K., G8081). After 4 hours, fluorescence (excitation wavelength of 560 nm/fluorescence wavelength of 590 nm) of each well was measured using EnVision™ (PerkinElmer Inc.). The effect of CDS-1 on recovery of AMP-dependently suppressed human T cell functions was evaluated based on the calculated $EC_{50}$ values using the IFNγ concentration and proliferation of human T cells as an index. In calculation of the $EC_{50}$ values, the ordinate represents an IFNγ concentration value or fluorescence value calculated from the measurement value, and the abscissa represents an antibody concentration value. In addition, a measurement value when the IFNγ concentration value can be determined to reach a convergence value according to the increase in the antibody concentration, from the shape of the sigmoid curve drawn on the graph, was set to 100%, and a measurement value when the IFNγ concentration value or fluorescence value can be determined to reach a convergence value according to the decrease in the antibody concentration therefrom was set to 0%. The $EC_{50}$ values were calculated from the 4-parameter logistic curve regression using the IFNγ concentration value and proliferation of human T cells as an index (Table 4). Among the compared subjects, the convergence value of CD73.4IgG2CS-IgG1.1f was lower than the convergence value of the IFNγ concentration value and the proliferation value of human T cells according to the increase in the antibody concentration of CDS-1, and MEDI9447 did not show a sigmoid curve, the EC50 values of MEDI9447 and CD73.4IgG2CS-IgG1.1f which can be compared with those of CDS-1 could not be calculated (FIG. 2 and FIG. 3).

TABLE 4

|  | $EC_{50}$ (ng/mL) | |
| --- | --- | --- |
|  | IFNγ | Proliferation of T cells |
| CDS-1 | 5.8 | 23.2 |
| 6E1 | 131.6 | 357.3 |

As a result, it was evident that CDS-1 has a stronger function of recovering AMP-dependently suppressed T cell functions than that of any one of antibodies of MEDI9447, 6E1, CD73.4IgG2CS-IgG1.1f, thereby activating anti-tumor immunity.

Example 6: Evaluation of Effect of CDS-3 and CDS-6 on Biological Activity of IL-7

In order to evaluate the effect of CDS-3 and CDS-6 acquired in Example 1 on the biological activity of IL-7, an assay was performed using a 2E8 cell line (ATCC:TIB-239) showing a dose-dependent cell proliferation activity due to the addition of human IL-7. In this example, Human IgG1 Isotype Control (EnzoLife Sciences Inc., ALX-804-133-C100) was used as a negative control. As a culture medium, Iscove's Modified Dulbecco's Medium (SIGMA-ALDRICH Corporation, 13390) containing L-glutamine solution (SIGMA-ALDRICH Corporation), 2-mercaptoethanol (Thermo Fisher Scientific Inc.), and inactivated 20% fetal bovine serum (HyClone Inc.) was used. A purified CDS-3, a purified CDS-6, or recombinant human IL-7 (Peprotech Inc., 200-07) was respectively added to a 384-well flat bottom plate (Thermo Fisher Scientific Inc.) by an amount of 10 µL/well. The purified CDS-3, the purified CDS-6, and the recombinant human IL-7 were diluted using a culture medium, the molecular weight of the purified CDS-3 and the purified CDS-6 was 180000, and the dilution was performed in 11 steps such that the final concentration was adjusted to 100 nM to 0.001 nM. A 2E8 cell was suspended in a culture medium, and added by an amount of 40 µL/well such that the final cell density was adjusted to $2\times10^4$ cells/well. Immediately thereafter, the resultant was cultured in a 5% $CO_2$ incubator at a temperature of 37° C. for 3 days. In order to analyze cell proliferation after 3 days, 50 µL/well of Cell-Titer-Glo Reagent was added to the above-described plate based on the protocol of CellTiter-Glo (trade name) Luminescent Cell Viability Assay (Promega K.K., G7573), and luminescent intensity of each well was measured using ARVO-HTS (PerkinElmer Inc.) On the basis of the measured luminescent intensity, the cell proliferation activity of the purified CDS-3, the purified CDS-6, and the recombinant human IL-7 were evaluated based on the calculated $EC_{50}$ values. In calculation of the $EC_{50}$ values, the ordinate represents luminescent intensity, and the abscissa represents a drug concentration value. In addition, a luminescent intensity value of 100 nM recombinant human IL-7 was set to 100%, and a luminescent intensity value of the negative control was set to 0% to draw a sigmoid curve. The $EC_{50}$ values of the purified CDS-3, the purified CDS-6, and the recombinant human IL-7 calculated from the 4-parameter logistic curve regression were 0.050 nM, 1.8 nM, and 0.051 nM.

As a result, it was evident that CDS-3 and CDS-6 have an effect on the biological activity of IL-7. In addition, it was evident that the effect of CDS-6 on biological activity of IL-7 is lower than that of CDS-3.

Example 7: Evaluation of Effect of CDS-7 and CDS-8 on Biological Activity of IL-21

In order to evaluate the effect of CDS-7 and CDS-8 acquired in Example 1 on the biological activity of IL-21, an assay was performed using a human cell line Ramos (ATCC: CRL-1596) in which STAT3 phosphorylation is human IL-21 concentration-dependently induced. A Ramos cell was sowed in a dish using an RPMI culture medium (SIGMA-ALDRICH Corporation, R8758), and cultured in a 5% $CO_2$ incubator at a temperature of 37° C. for 16 hours. After being collected, the Ramos cell was suspended in the above-described culture medium and sowed in a 96-well plate (Nippon Genetics Co., Ltd., 35800) by an amount of 45 µL/well such that the final cell density was adjusted to $2\times10^5$ cells, and a purified CDS-7, a purified CDS-8, or recombinant human IL-21 (Peprotech Inc., 200-21) was respectively added thereto by an amount of 5 µL/well to be reacted. The purified CDS-7, the purified CDS-8, or the recombinant human IL-21 was diluted using PBS (Life Technologies, Inc.), the molecular weight of the purified CDS-7 and the purified CDS-8 was 180000, and the dilution was performed in 11 steps such that the final concentration was adjusted to 1200 nM to 0.02 nM, or performed in 10 steps such that the final concentration was adjusted to 400 nM to 0.02 nM. After being reacted at a temperature of 37° C. for 30 minutes, the entire amount was transferred to a 96-well round bottom plate (Corning Inc., 351177) to which 200 µL/well of Fix Buffer I (BD Biosciences, Inc., 557870) had been added in advance, and reacted at a temperature of 37° C. for 10 minutes to fix the cells. After washing was performed with a dyeing buffer, 200 µL/well of Perm Buffer III (BD Biosciences, Inc., 558050) was added thereto, reacted on ice for 30 minutes for permeabilization. As the dyeing buffer, Stain Buffer (FBS) (BD Biosciences, Inc., 554656) was used. The resultant was washed with the above-described dyeing buffer and suspended, phosphorylated STAT3 was dyed using PE Mouse Anti-Stat3 (pY705) (BD Biosciences, Inc., 562072), and then fluorescence intensity of the cell was measured using FACSArray™ (BD Biosciences, Inc.). As the fluorescence intensity, a Geometric MFI value was used. On the basis of the measured fluorescence intensity, $EC_{50}$ values of the purified CDS-7, the purified CDS-8, and the recombinant human IL-21 were measured, and the STAT3 phosphorylation-induced activity was evaluated. In calculation of the $EC_{50}$ values, the ordinate represents measured fluorescence intensity, and the abscissa represents a drug concentration value. In addition, a fluorescence intensity value that can be determined to reach a convergence value according to the increase in the drug concentration, from the shape of the sigmoid curve drawn on the graph, was set to 100%, and a fluorescence intensity value that can be determined to reach a convergence value according to the decrease in the drug concentration therefrom was set to 0%. The $EC_{50}$ values of the purified CDS-7, the purified CDS-8, and the recombinant human IL-21 calculated from the 4-parameter logistic curve regression were 1.3 nM, 28.3 nM, and 8.0 nM.

As a result, it was evident that CDS-7 and CDS-8 have an effect on the biological activity of IL-21. In addition, it was evident that the effect of CDS-8 on the biological activity of IL-21 is lower than that of CDS-7.

INDUSTRIAL APPLICABILITY

The anti-human CD73 antibody and fused form of the present invention is expected to be useful for preventing or treating cancer. In addition, the method for producing a polynucleotide, an expression vector, a transformed host cell, or an antibody of the present invention is useful for producing the anti-human CD73 antibody and fused form.

SEQUENCE LIST FREE TEXT

In the number heading <223> of the following sequence list, description of "Artificial Sequence" is made. Specifically, the base sequences shown by SEQ ID NOS: 1 and 3 of the sequence list are respectively the base sequences encoding the residue number 1 of a variable region to the C terminal of a constant region according to Kabat numbering, of the heavy chain and the light chain of the CDS-1, the amino acid sequences shown by SEQ ID NOS: 2 and 4 of the sequence list are respectively the amino acid sequences of the heavy chain and the light chain encoded by SEQ ID NOS: 1 and 3, the base sequence shown by SEQ ID NO: 5 or 6 of the sequence list is the base sequence encoding the residue number 1 of a variable region to the C terminal of a constant region according to Kabat numbering and human IL-7 via a linker, of the heavy chain of CDS-3, and the amino acid sequence shown by SEQ ID NO: 7 of the sequence list is the amino acid sequence of the heavy chain encoded by SEQ ID NO: 5 or 6. The base sequence shown by SEQ ID NO: 8 is the base sequence encoding the residue number 1 of a variable region to the C terminal of a constant region according to Kabat numbering, of the light chain of CDS-3. The base sequence shown by SEQ ID NO: 9 or 16 of the sequence list is the base sequence encoding the residue number 1 of a variable region to the C terminal of a constant region according to Kabat numbering and a human IL-7 variant, of the heavy chain of CDS-6, the amino acid sequence shown by SEQ ID NO: 10 of the sequence list is the amino acid sequence of the heavy chain encoded by SEQ ID NO: 9 or 16. The base sequence shown by SEQ ID NO: 11 of the sequence list is the base sequence encoding the residue number 1 of a variable region to the C terminal of a constant region according to Kabat numbering, of the heavy chain of CDS-7. The base sequence shown by SEQ ID NO: 12 of the sequence list is the base sequence encoding the residue number 1 of a variable region to the C terminal of a constant region according to Kabat numbering and human IL-21 via a linker, of the light chain of CDS-7, and the amino acid sequence shown by SEQ ID NO: 13 of the sequence list is the amino acid sequence of the light chain encoded by SEQ ID NO: 12. The base sequence shown by SEQ ID NO: 14 of the sequence list is the base sequence encoding the residue number 1 of a variable region to the C terminal of a constant region according to Kabat numbering and a human IL-21 variant via a linker, of the light chain of CDS-8, and the amino acid sequence shown by SEQ ID NO: 15 of the sequence list is the amino acid sequence of the light chain encoded by SEQ ID NO: 14.

The invention claimed is:

1. An anti-human CD73 antibody or an antigen-binding fragment thereof comprising:
    a heavy chain variable region comprising CDR1 consisting of amino acid numbers 31 to 35 of SEQ ID NO: 2, CDR2 consisting of amino acid numbers 50 to 66 of SEQ ID NO: 2, and CDR3 consisting of amino acid numbers 99 to 112 of SEQ ID NO: 2; and
    a light chain variable region comprising CDR1 consisting of amino acid numbers 24 to 34 of SEQ ID NO: 4, CDR2 consisting of amino acid numbers of 50 to 56 of SEQ ID NO: 4, and CDR3 consisting of amino acid numbers 89 to 98 of SEQ ID NO: 4.

2. The anti-human CD73 antibody according to claim 1, comprising a heavy chain consisting of SEQ ID NO: 2 and a light chain consisting of SEQ ID NO: 4.

3. A modified form in which the anti-human CD73 antibody or the antigen-binding fragment thereof according to claim 1 is bound to a modifying agent.

4. The anti-human CD73 antibody according to claim 1, selected from the group consisting of:
    (a) an anti-human CD73 antibody comprising a heavy chain consisting of SEQ ID NO: 2 and a light chain consisting of SEQ ID NO: 4 and further comprising a posttranslational modification; and
    (b) an anti-human CD73 antibody comprising a heavy chain consisting of amino acid numbers 1-452 of SEQ ID NO: 2 and a light chain consisting of SEQ ID NO: 4.

5. The anti-human CD73 antibody according to claim 4, comprising the heavy chain consisting of SEQ ID NO: 2, and the light chain consisting of SEQ ID NO: 4.

6. The anti-human CD73 antibody according to claim 4, comprising the heavy chain consisting of amino acid numbers 1 to 452 of SEQ ID NO: 2, and the light chain consists of SEQ ID NO: 4.

7. A pharmaceutical composition comprising the anti-human CD73 antibody according to claim 4, and a pharmaceutically acceptable excipient.

8. A method for treating cancer, comprising administering to a subject with cancer a therapeutically effective amount of the anti-human CD73 antibody according to claim 4.

9. The anti-human CD73 antibody or the antigen-binding fragment thereof according to claim 1, comprising a heavy chain variable region consisting of amino acid numbers 1 to 123 of SEQ ID NO: 2, and a light chain variable region consisting of amino acid numbers 1 to 109 of SEQ ID NO: 4.

10. A polynucleotide comprising a sequence encoding a heavy chain variable region or a light chain variable region of the antibody or the antigen-binding fragment thereof according to claim 9.

11. The polynucleotide according to claim 10, selected from the group consisting of:
a polynucleotide comprising a sequence encoding SEQ ID NO: 2; and
a polynucleotide comprising a sequence encoding SEQ ID NO: 4.

12. An expression vector comprising a polynucleotide comprising a sequence encoding a heavy chain variable region or a light chain variable region of the antibody or the antigen-binding fragment thereof according to claim 9.

13. The expression vector according to claim 12, comprising:
a polynucleotide comprising a sequence encoding SEQ ID NO: 2; and/or
a polynucleotide comprising a sequence encoding SEQ ID NO: 4.

14. A host cell selected from the group consisting of:
a host cell transformed with an expression vector comprising a polynucleotide comprising a sequence encoding a heavy chain variable region of the antibody or the antigen-binding fragment thereof according to claim 9;
a host cell transformed with an expression vector comprising a polynucleotide comprising a sequence encoding a light chain variable region of the antibody or the antigen-binding fragment thereof according to claim 9;
a host cell transformed with an expression vector comprising a polynucleotide comprising a sequence encoding a heavy chain variable region of the antibody or the antigen-binding fragment thereof according to claim 9 and a polynucleotide comprising a sequence encoding a light chain variable region of the antibody or the antigen-binding fragment thereof according to claim 9; and
a host cell transformed with an expression vector comprising a polynucleotide comprising a sequence encoding a heavy chain variable region of the antibody or the antigen-binding fragment thereof according to claim 9 and an expression vector comprising a polynucleotide comprising a sequence encoding a light chain variable region of the antibody or the antigen-binding fragment thereof according to claim 9.

15. The host cell according to claim 14, selected from the group consisting of:
a host cell transformed with an expression vector comprising a polynucleotide comprising a sequence encoding SEQ ID NO: 2;
a host cell transformed with an expression vector comprising a polynucleotide comprising a sequence encoding SEQ ID NO: 4;
a host cell transformed with an expression vector comprising a polynucleotide comprising a sequence encoding SEQ ID NO: 2 and a polynucleotide comprising a sequence encoding SEQ ID NO: 4; and
a host cell transformed with an expression vector comprising a polynucleotide comprising a sequence encoding SEQ ID NO: 2 and an expression vector comprising a polynucleotide comprising a sequence encoding SEQ ID NO: 4.

16. A method for producing an anti-human CD73 antibody, an antigen-binding fragment thereof, or a fused form of any one thereof, the method comprising:
culturing a host cell selected from the group consisting of the following (a) to (c) to express an anti-human CD73 antibody, an antigen-binding fragment thereof, or a fused form of any one thereof:
(a) a host cell transformed with an expression vector comprising a polynucleotide comprising a base sequence encoding a heavy chain variable region of the antibody or the antigen-binding fragment thereof according to claim 9 and a polynucleotide comprising a base sequence encoding a light chain variable region of the antibody or the antigen-binding fragment thereof according to claim 9;
(b) a host cell transformed with an expression vector comprising a polynucleotide comprising a base sequence encoding a heavy chain variable region of the antibody or the antigen-binding fragment thereof according to claim 9 and an expression vector comprising a polynucleotide comprising a base sequence encoding a light chain variable region of the antibody or the antigen-binding fragment thereof according to claim 9; and
(c) a host cell transformed with an expression vector comprising a polynucleotide comprising a base sequence encoding a heavy chain variable region of the antibody or the antigen-binding fragment thereof according to claim 9 and a host cell transformed with an expression vector comprising a polynucleotide comprising a base sequence encoding a light chain variable region of the antibody or the antigen-binding fragment thereof according to claim 9.

17. A fused form in which the anti-human CD73 antibody or the antigen-binding fragment thereof according to claim 1 is fused with another peptide or protein.

18. The fused form according to claim 17, selected from the group consisting of the following (a) to (e):
(a) a fused form comprising a heavy chain consisting of SEQ ID NO: 7 or an amino acid sequence in which the lysine at position 453 of SEQ ID NO: 7 has been removed, and a light chain consisting of SEQ ID NO: 4;
(b) a fused form comprising a heavy chain consisting of SEQ ID NO: 10 or an amino acid sequence in which the lysine at position 453 of SEQ ID NO: 10 has been removed, and a light chain consisting of SEQ ID NO: 4;
(c) a fused form comprising a heavy chain comprising amino acid numbers 1-452 of SEQ ID NO: 2 and a light chain consisting of SEQ ID NO: 13;
(d) a fused form comprising a heavy chain comprising amino acid numbers 1-452 of SEQ ID NO: 2 and a light chain consisting of SEQ ID NO: 15; and (e) a fused form of (a) to (d) further comprising a posttranslational modification.

19. A polynucleotide encoding a heavy chain or a light chain of a fused form according to claim 18.

20. An expression vector encoding a heavy chain or a light chain of a fused form according to claim 18.

21. A host cell selected from the group consisting of:
a host cell transformed with an expression vector comprising a polynucleotide comprising a sequence encoding a heavy chain of the fused form according to claim 18;
a host cell transformed with an expression vector comprising a polynucleotide comprising a sequence encoding a light chain of the fused form according to claim 18;
a host cell transformed with an expression vector comprising a polynucleotide comprising a sequence encoding a heavy chain of the fused form according to claim 18 and a polynucleotide comprising a sequence encoding a light chain of the fused form according to claim 18; and
a host cell transformed with an expression vector comprising a polynucleotide comprising a sequence encoding a heavy chain of the fused form according to claim 18 and an expression vector comprising a polynucleotide comprising a sequence encoding a light chain of the fused form according to claim 18.

22. A method for producing a fused form of an anti-human CD73 antibody comprising:
culturing a host cell selected from the group consisting of the following (a) to (c) to express a fused form of an anti-human CD73 antibody:
(a) a host cell transformed with an expression vector comprising a polynucleotide comprising a base sequence encoding a heavy chain of the fused form according to claim 18 and a polynucleotide comprising a base sequence encoding a light chain of the fused form according to claim 18;
(b) a host cell transformed with an expression vector comprising a polynucleotide comprising a base sequence encoding a heavy chain of the fused form according to claim 18 and an expression vector comprising a polynucleotide comprising a base sequence encoding a light chain of the fused form according to claim 18; and (c) a host cell transformed with an expression vector comprising a polynucleotide comprising a base sequence encoding a heavy chain of the fused form according to claim 18 and a host cell transformed with an expression vector comprising a polynucleotide comprising a base sequence encoding a light chain of the fused form according to claim 18.

23. A pharmaceutical composition comprising the fused form according to claim 18, and a pharmaceutically acceptable excipient.

24. A method for treating cancer, comprising administering to a subject with cancer a therapeutically effective amount of the fused form according to claim 18.

25. A method for producing an anti-human CD73 antibody or a fused form thereof, comprising:
culturing a host cell selected from the group consisting of the following (a) to (c) to express an anti-human CD73 antibody or a fused form thereof:
(a) a host cell transformed with an expression vector comprising a polynucleotide comprising a base sequence encoding SEQ ID NO: 2 and a polynucleotide comprising a base sequence encoding SEQ ID NO: 4;
(b) a host cell transformed with an expression vector comprising a polynucleotide comprising a base sequence encoding SEQ ID NO: 2 and an expression vector comprising a polynucleotide comprising a base sequence encoding SEQ ID NO: 4; and
(c) a host cell transformed with an expression vector comprising a polynucleotide comprising a base sequence encoding SEQ ID NO: 2 and a host cell transformed with an expression vector comprising a polynucleotide comprising a base sequence encoding SEQ ID NO: 4.

* * * * *

SEQUENCE LISTING

```
<160> NUMBER OF SEQ ID NOS: 16

<210> SEQ ID NO 1
<211> LENGTH: 1362
<212> TYPE: DNA
<213> ORGANISM: Artificial Sequence
<220> FEATURE:
<223> OTHER INFORMATION: H-chain of anti-human CD73 antibody
<220> FEATURE:
<221> NAME/KEY: CDS
<222> LOCATION: (1)..(1362)

<400> SEQUENCE: 1 gag gtg cag ttg gtc gaa agt ggc gga gga ctc gta cag cca ggt ggg        48
Glu Val Gln Leu Val Glu Ser Gly Gly Gly Leu Val Gln Pro Gly Gly
1               5                  10                  15 tca ctg cgt ctg tcc tgt gct gca tct ggg ttt acc ttc gat gac tat        96
Ser Leu Arg Leu Ser Cys Ala Ala Ser Gly Phe Thr Phe Asp Asp Tyr
            20                  25                  30 gcc atg cac tgg gtt cga caa gct cct ggc aaa ggc ctt gaa tgg gtg       144
Ala Met His Trp Val Arg Gln Ala Pro Gly Lys Gly Leu Glu Trp Val
        35                  40                  45 agt ggg atc aac tgg aat agc gac aac atc gac tat gcc gac tct gtg       192
Ser Gly Ile Asn Trp Asn Ser Asp Asn Ile Asp Tyr Ala Asp Ser Val
    50                  55                  60 aaa ggc cgc ttt acc att agc cgg gat aac tcc aag aac act ctg tat       240
Lys Gly Arg Phe Thr Ile Ser Arg Asp Asn Ser Lys Asn Thr Leu Tyr
65                  70                  75                  80 ctg cag atg aat agc ctc aga gca gag gat aca gcc gtc tac tac tgc       288
Leu Gln Met Asn Ser Leu Arg Ala Glu Asp Thr Ala Val Tyr Tyr Cys
                85                  90                  95 gcc aag gat agg agg aag tac tcc aat tct ccc ggt gct ttc gac ata       336
Ala Lys Asp Arg Arg Lys Tyr Ser Asn Ser Pro Gly Ala Phe Asp Ile
            100                 105                 110 tgg ggt cag gga aca ctg gtt act gtg tcc tca gcc tcc acc aag ggc       384
Trp Gly Gln Gly Thr Leu Val Thr Val Ser Ser Ala Ser Thr Lys Gly
        115                 120                 125 cca tcg gtc ttc ccc ctg gca ccc tcc tcc aag agc acc tct ggg ggc       432
Pro Ser Val Phe Pro Leu Ala Pro Ser Ser Lys Ser Thr Ser Gly Gly
    130                 135                 140 aca gcg gcc ctg ggc tgc ctg gtc aag gac tac ttc ccc gaa ccg gtg       480
Thr Ala Ala Leu Gly Cys Leu Val Lys Asp Tyr Phe Pro Glu Pro Val
145                 150                 155                 160 acg gtg tcg tgg aac tca ggc gcc ctg acc agc ggc gtg cac acc ttc       528
Thr Val Ser Trp Asn Ser Gly Ala Leu Thr Ser Gly Val His Thr Phe
                165                 170                 175 ccg gct gtc cta cag tcc tca gga ctc tac tcc ctt agt agc gtg gtg       576
Pro Ala Val Leu Gln Ser Ser Gly Leu Tyr Ser Leu Ser Ser Val Val
            180                 185                 190 acc gtg ccc tcc agc agc ttg ggc acc cag acc tac atc tgc aac gtg       624
Thr Val Pro Ser Ser Ser Leu Gly Thr Gln Thr Tyr Ile Cys Asn Val
        195                 200                 205 aat cac aag ccc agc aac acc aag gtg gac aag aaa gtt gag ccc aaa       672
```

```
                Asn His Lys Pro Ser Asn Thr Lys Val Asp Lys Lys Val Glu Pro Lys
                    210                 215                 220 tct tgt gac aaa act cac aca tgc cca ccg tgc cca gca cct gaa gcc        720
Ser Cys Asp Lys Thr His Thr Cys Pro Pro Cys Pro Ala Pro Glu Ala
225                 230                 235                 240 gct ggg gga ccg tca gtc ttc ctc ttc ccc cca aaa ccc aag gac acc        768
Ala Gly Gly Pro Ser Val Phe Leu Phe Pro Pro Lys Pro Lys Asp Thr
                245                 250                 255 ctc atg atc tcc cgg acc cct gag gtc aca tgc gtg gtg gtg gac gtg        816
Leu Met Ile Ser Arg Thr Pro Glu Val Thr Cys Val Val Val Asp Val
            260                 265                 270 agc cac gaa gac cct gag gtc aag ttc aac tgg tac gtg gac ggc gtg        864
Ser His Glu Asp Pro Glu Val Lys Phe Asn Trp Tyr Val Asp Gly Val
        275                 280                 285 gag gtg cat aat gcc aag aca aag ccg cgg gag gag cag tac aac agc        912
Glu Val His Asn Ala Lys Thr Lys Pro Arg Glu Glu Gln Tyr Asn Ser
    290                 295                 300 acg tac cgt gtg gtc agc gtc ctc acc gtc ctg cac cag gac tgg ctg        960
Thr Tyr Arg Val Val Ser Val Leu Thr Val Leu His Gln Asp Trp Leu
305                 310                 315                 320 aat ggc aag gag tac aag tgc aag gtc tcc aac aaa gcc ctc cca gcc       1008
Asn Gly Lys Glu Tyr Lys Cys Lys Val Ser Asn Lys Ala Leu Pro Ala
                325                 330                 335 agc atc gag aaa acc atc tcc aaa gcc aaa ggg cag ccc cga gaa cca       1056
Ser Ile Glu Lys Thr Ile Ser Lys Ala Lys Gly Gln Pro Arg Glu Pro
                340                 345                 350 cag gtg tac acc ctg ccc cca tcc cgg gat gag ctg acc aag aac cag       1104
Gln Val Tyr Thr Leu Pro Pro Ser Arg Asp Glu Leu Thr Lys Asn Gln
            355                 360                 365 gtc agc ctg acc tgc ctg gtc aaa ggc ttc tat ccc agc gac atc gcc       1152
Val Ser Leu Thr Cys Leu Val Lys Gly Phe Tyr Pro Ser Asp Ile Ala
        370                 375                 380 gtg gag tgg gag agc aat ggg cag ccg gag aac aac tac aag acc acg       1200
Val Glu Trp Glu Ser Asn Gly Gln Pro Glu Asn Asn Tyr Lys Thr Thr
385                 390                 395                 400 cct ccc gtg ctg gac tcc gac ggc tcc ttc ttc ctc tac agc aag ctc       1248
Pro Pro Val Leu Asp Ser Asp Gly Ser Phe Phe Leu Tyr Ser Lys Leu
                405                 410                 415 acc gtg gac aag agc agg tgg cag cag ggg aac gtc ttc tca tgc tcc       1296
Thr Val Asp Lys Ser Arg Trp Gln Gln Gly Asn Val Phe Ser Cys Ser
                420                 425                 430 gtg atg cat gag gct ctg cac aac cac tac acg cag aag agc ctc tcc       1344
Val Met His Glu Ala Leu His Asn His Tyr Thr Gln Lys Ser Leu Ser
            435                 440                 445 ctg tct ccg ggt aaa tga                                                1362
Leu Ser Pro Gly Lys
        450

<210> SEQ ID NO 2
<211> LENGTH: 453
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30
```

```
Ala Met His Trp Val Arg Gln Ala Pro Gly Lys Gly Leu Glu Trp Val
         35                  40                  45

Ser Gly Ile Asn Trp Asn Ser Asp Asn Ile Asp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Asp Arg Arg Lys Tyr Ser Asn Ser Pro Gly Ala Phe Asp Ile
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
```

<210> SEQ ID NO 3
<211> LENGTH: 648
<212> TYPE: DNA
<213> ORGANISM: Artificial Sequence
<220> FEATURE:
<223> OTHER INFORMATION: L-chain of anti-human CD73 antibody
<220> FEATURE:
<221> NAME/KEY: CDS
<222> LOCATION: (1)..(648)

<400> SEQUENCE: 3

```
gac ata cag atg act cag tca ccc agt tcc ctt tct gcc agt gtg gga        48
Asp Ile Gln Met Thr Gln Ser Pro Ser Ser Leu Ser Ala Ser Val Gly
1               5                   10                  15 gat agg gtc act atc acc tgt aga gcc agc cag atc att ggc cca tgg        96
Asp Arg Val Thr Ile Thr Cys Arg Ala Ser Gln Ile Ile Gly Pro Trp
            20                  25                  30 ttg gct tgg tat cag cag aaa cca ggg aaa gca ccc aag ctg ctc atc       144
Leu Ala Trp Tyr Gln Gln Lys Pro Gly Lys Ala Pro Lys Leu Leu Ile
        35                  40                  45 tat cga gct tcc tct ctg gaa tcc ggt gtt cct tcc cgc ttt agc ggt       192
Tyr Arg Ala Ser Ser Leu Glu Ser Gly Val Pro Ser Arg Phe Ser Gly
    50                  55                  60 tca ggg agt gga acc gac ttc aca ctg acc att agc tct ctg caa cct       240
Ser Gly Ser Gly Thr Asp Phe Thr Leu Thr Ile Ser Ser Leu Gln Pro
65                  70                  75                  80 gag gat ttc gcc acg tac tac tgc cag cag tac aac agc tat tct ccc       288
Glu Asp Phe Ala Thr Tyr Tyr Cys Gln Gln Tyr Asn Ser Tyr Ser Pro
                85                  90                  95 tgg aca ttt ggc caa ggc aca aag gtg gag atc aag cgg act gtg gct       336
Trp Thr Phe Gly Gln Gly Thr Lys Val Glu Ile Lys Arg Thr Val Ala
            100                 105                 110 gca cca tct gtc ttc atc ttc ccg cca tct gat gag cag ttg aaa tct       384
Ala Pro Ser Val Phe Ile Phe Pro Pro Ser Asp Glu Gln Leu Lys Ser
        115                 120                 125 gga act gcc tct gtt gtg tgc ctg ctg aat aac ttc tat ccc aga gag       432
Gly Thr Ala Ser Val Val Cys Leu Leu Asn Asn Phe Tyr Pro Arg Glu
    130                 135                 140 gcc aaa gta cag tgg aag gtg gat aac gcc ctc caa tcg ggt aac tcc       480
Ala Lys Val Gln Trp Lys Val Asp Asn Ala Leu Gln Ser Gly Asn Ser
145                 150                 155                 160 cag gag agt gtc aca gag cag gac agc aag gac agc acc tac agc ctc       528
Gln Glu Ser Val Thr Glu Gln Asp Ser Lys Asp Ser Thr Tyr Ser Leu
                165                 170                 175 agc agc acc ctg acg ctg agc aaa gca gac tac gag aaa cac aaa gtc       576
Ser Ser Thr Leu Thr Leu Ser Lys Ala Asp Tyr Glu Lys His Lys Val
            180                 185                 190 tac gcc tgc gaa gtc acc cat cag ggc ctg agc tcg ccc gtc aca aag       624
Tyr Ala Cys Glu Val Thr His Gln Gly Leu Ser Ser Pro Val Thr Lys
        195                 200                 205 agc ttc aac agg gga gag tgt tag                                       648
Ser Phe Asn Arg Gly Glu Cys
    210                 215
```

<210> SEQ ID NO 4
<211> LENGTH: 215
<212> TYPE: PRT
<213> ORGANISM: Artificial Sequence
<220> FEATURE:
<223> OTHER INFORMATION: Synthetic Construct -continued

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Gly Pro Trp
            20                  25                  30

Leu Ala Trp Tyr Gln Gln Lys Pro Gly Lys Ala Pro Lys Leu Leu Ile
        35                  40                  45

Tyr Arg Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 5
<211> LENGTH: 1848
<212> TYPE: DNA
<213> ORGANISM: Artificial Sequence
<220> FEATURE:
<223> OTHER INFORMATION: H-chain of fused form of anti-human CD73
      antibody and IL-7

<400> SEQUENCE: 5

```
gaagtacagt tggtcgaaag cggaggaggg ctggttcagc ctggcggctc actcagactg      60
tcatgcgctg cctctgggtt tacattcgac gattatgcca tgcattgggt acgacaggca     120
ccaggcaaag ggctggagtg ggtttctggg attaactgga atagcgataa tatcgactat     180
gccgactctg taaaggggcg ctttactatc agtcgggaca atagtaagaa tacgctctat     240
ctgcagatga atagcctgag agcagaagat accgctgtgt actactgtgc caaagaccgg     300
cgtaagtaca gtaactctcc tggtgccttt gacatctggg gacagggcac tcttgttacc     360
gtgagcagcg catctaccaa aggtccctca gtctttcccc tcgctcctag ttctaagtcc     420
acatcaggtg gaactgccgc tttgggttgc ctggtaaagg actactttcc cgagcctgtt     480
acagtgagct ggaactccgg agctctgaca tccggtgtgc acacatttcc tgccgttctt     540
cagtcctcag ggctgtattc cttgtcctca gtggttacag tgcccagcag tagtctgggg     600
acacagacat acatttgcaa tgtgaatcac aagccaagta acactaaggt cgataagaag     660
gtcgagccca aaagttgcga taagacccat acttgtccac cttgtcctgc tcctgaggcc     720
```

```
gcaggaggcc cttctgtgtt cctgtttcca cccaaaccca aggacactct gatgattagc    780
cggacgccag aggtgacctg tgttgtggtt gatgtctctc acgaggaccc agaagtgaaa    840
ttcaactggt acgtcgacgg cgtggaagtg cacaatgcca aaaccaagcc acgcgaggag    900
cagtacaaca gcacctatcg ggtggtgagc gtgttgactg tgctgcatca agattggctg    960
aatggaaagg agtacaagtg taaggtgtct aacaaggcac tgcccgcaag catcgaaaag   1020
accatcagta aggctaaggg ccagcccagg gaaccacagg tctacaccct gccaccttcc   1080
cgtgacgagt tgaccaagaa ccaggtgtca cttacgtgct ggtgaaaggc ttctatccc    1140 tccgacattg ccgtagaatg ggaaagcaat gggcaacccg agaataacta caaaacaact   1200
ccacccgtcc ttgattctga cggttccttc ttcctctatt ccaaactgac tgtcgataaa   1260
tctcgatggc aacagggcaa tgtcttttct tgtagtgtga tgcatgaagc attgcataac   1320
cactacaccc agaagtccct gtctttgtcc cctgggaaag gaggcggtgg atccggtggt   1380
ggcggctcag attgcgacat agaaggcaag gacggcaaac agtatgagtc cgtcctgatg   1440
gtgtccattg atcagctgct ggattctatg aaggaaatcg gaagcaactg cctgaacaat   1500
gagtttaact tcttcaaacg acacatctgt gatgccaaca aagagggcat gtttctcttc   1560
agagccgcta ggaaactgag gcagtttctc aagatgaact ccactggcga cttcgatctg   1620
caccttctga aggtatcaga ggggaccaca atactgctga actgcaccgg ccaagtcaag   1680
ggtcgcaagc ccgctgccct tggagaagct caacccacca aaagcctgga agagaacaaa   1740
tccctcaagg agcagaagaa actcaacgac ctgtgctttc tcaagaggct ccttcaggag   1800
attaagacct gttggaataa gatccttatg gggacaaaag agcactga               1848
```

<210> SEQ ID NO 6
<211> LENGTH: 1848
<212> TYPE: DNA
<213> ORGANISM: Artificial Sequence
<220> FEATURE:
<223> OTHER INFORMATION: H-chain of fused form of anti-human CD73
      antibody and IL-7
<220> FEATURE:
<221> NAME/KEY: CDS
<222> LOCATION: (1)..(1848)

<400> SEQUENCE: 6

```
gaa gtg cag ctg gtg gaa tct ggc ggc gga ctg gtg cag cct ggc gga     48
Glu Val Gln Leu Val Glu Ser Gly Gly Gly Leu Val Gln Pro Gly Gly
1               5                   10                  15 tct ctg aga ctg tct tgt gcc gcc tcc ggc ttc acc ttc gac gac tac     96
Ser Leu Arg Leu Ser Cys Ala Ala Ser Gly Phe Thr Phe Asp Asp Tyr
            20                  25                  30 gct atg cac tgg gtg cga cag gcc cct ggc aag gga ctg gaa tgg gtg    144
Ala Met His Trp Val Arg Gln Ala Pro Gly Lys Gly Leu Glu Trp Val
        35                  40                  45 tcc ggc atc aac tgg aac tcc gac aac atc gac tac gcc gac tcc gtg    192
Ser Gly Ile Asn Trp Asn Ser Asp Asn Ile Asp Tyr Ala Asp Ser Val
    50                  55                  60 aag ggc cgg ttc acc atc tcc cgg gac aac tcc aag aac acc ctg tac    240
Lys Gly Arg Phe Thr Ile Ser Arg Asp Asn Ser Lys Asn Thr Leu Tyr
65                  70                  75                  80 ctg cag atg aac tcc ctg cgg gcc gag gac acc gcc gtg tac tac tgc    288
Leu Gln Met Asn Ser Leu Arg Ala Glu Asp Thr Ala Val Tyr Tyr Cys
                85                  90                  95 gcc aag gac cgg cgg aag tac tcc aac tct cct ggc gcc ttc gac atc    336
Ala Lys Asp Arg Arg Lys Tyr Ser Asn Ser Pro Gly Ala Phe Asp Ile
            100                 105                 110
```

```
tgg ggc cag ggc aca ctc gtg acc gtg tcc tct gct tcc acc aag ggc      384
Trp Gly Gln Gly Thr Leu Val Thr Val Ser Ser Ala Ser Thr Lys Gly
            115                 120                 125 ccc tcc gtg ttt cct ctg gcc cct tcc agc aag tcc acc tct ggc gga      432
Pro Ser Val Phe Pro Leu Ala Pro Ser Ser Lys Ser Thr Ser Gly Gly
130                 135                 140 aca gcc gct ctg ggc tgc ctc gtg aag gac tac ttc ccc gag ccc gtg      480
Thr Ala Ala Leu Gly Cys Leu Val Lys Asp Tyr Phe Pro Glu Pro Val
145                 150                 155                 160 aca gtg tct tgg aac tct ggc gcc ctg act tct ggc gtg cac acc ttc      528
Thr Val Ser Trp Asn Ser Gly Ala Leu Thr Ser Gly Val His Thr Phe
                165                 170                 175 cct gct gtg ctg cag tct agc ggc ctg tac tcc ctg tcc tcc gtc gtg      576
Pro Ala Val Leu Gln Ser Ser Gly Leu Tyr Ser Leu Ser Ser Val Val
            180                 185                 190 act gtg ccc tcc agc tct ctg ggc acc cag acc tac atc tgc aac gtg      624
Thr Val Pro Ser Ser Ser Leu Gly Thr Gln Thr Tyr Ile Cys Asn Val
            195                 200                 205 aac cac aag ccc tcc aac acc aag gtg gac aag aag gtg gaa ccc aag      672
Asn His Lys Pro Ser Asn Thr Lys Val Asp Lys Lys Val Glu Pro Lys
210                 215                 220 tcc tgc gac aag acc cac acc tgt ccc cct tgt cct gcc cct gaa gct      720
Ser Cys Asp Lys Thr His Thr Cys Pro Pro Cys Pro Ala Pro Glu Ala
225                 230                 235                 240 gct ggc ggc cct tct gtg ttt ctg ttc ccc cca aag cct aag gac acc      768
Ala Gly Gly Pro Ser Val Phe Leu Phe Pro Pro Lys Pro Lys Asp Thr
                245                 250                 255 ctg atg atc tcc cgg acc ccc gaa gtg acc tgc gtg gtg gtg gat gtg      816
Leu Met Ile Ser Arg Thr Pro Glu Val Thr Cys Val Val Val Asp Val
            260                 265                 270 tcc cac gag gac cct gaa gtg aag ttc aat tgg tac gtg gac ggc gtg      864
Ser His Glu Asp Pro Glu Val Lys Phe Asn Trp Tyr Val Asp Gly Val
            275                 280                 285 gaa gtg cac aac gcc aag acc aag cct aga gag gaa cag tac aac tcc      912
Glu Val His Asn Ala Lys Thr Lys Pro Arg Glu Glu Gln Tyr Asn Ser
290                 295                 300 acc tac cgg gtg gtg tcc gtg ctg acc gtg ctg cat cag gac tgg ctg      960
Thr Tyr Arg Val Val Ser Val Leu Thr Val Leu His Gln Asp Trp Leu
305                 310                 315                 320 aac ggc aaa gag tac aag tgc aag gtg tcc aac aag gcc ctg ccc gcc     1008
Asn Gly Lys Glu Tyr Lys Cys Lys Val Ser Asn Lys Ala Leu Pro Ala
                325                 330                 335 tcc atc gaa aag acc atc tcc aag gcc aag ggc cag ccc cgg gaa ccc     1056
Ser Ile Glu Lys Thr Ile Ser Lys Ala Lys Gly Gln Pro Arg Glu Pro
            340                 345                 350 cag gtg tac aca ctg ccc cct agc agg gac gag ctg acc aag aac cag     1104
Gln Val Tyr Thr Leu Pro Pro Ser Arg Asp Glu Leu Thr Lys Asn Gln
            355                 360                 365 gtg tcc ctg acc tgt ctc gtg aaa ggc ttc tac ccc tcc gat atc gcc     1152
Val Ser Leu Thr Cys Leu Val Lys Gly Phe Tyr Pro Ser Asp Ile Ala
            370                 375                 380 gtg gaa tgg gag agc aac ggc cag ccc gag aac aac tat aag acc acc     1200
Val Glu Trp Glu Ser Asn Gly Gln Pro Glu Asn Asn Tyr Lys Thr Thr
385                 390                 395                 400 ccc cct gtg ctg gac tcc gac ggc tca ttc ttt ctg tac tcc aag ctg     1248
Pro Pro Val Leu Asp Ser Asp Gly Ser Phe Phe Leu Tyr Ser Lys Leu
                405                 410                 415 aca gtg gac aag tcc cgg tgg cag cag ggc aac gtg ttc tcc tgc agc     1296
Thr Val Asp Lys Ser Arg Trp Gln Gln Gly Asn Val Phe Ser Cys Ser
```

```
gtg atg cac gag gcc ctg cac aac cac tac acc cag aag tcc ctg tcc      1344
Val Met His Glu Ala Leu His Asn His Tyr Thr Gln Lys Ser Leu Ser
    435                 440                 445 ctg tct ccc gga aaa ggc ggc gga gga tcc ggc gga ggc gga tct gat      1392
Leu Ser Pro Gly Lys Gly Gly Gly Gly Ser Gly Gly Gly Gly Ser Asp
450                 455                 460 tgt gac atc gag ggc aag gac ggc aag cag tac gag agc gtg ctg atg      1440
Cys Asp Ile Glu Gly Lys Asp Gly Lys Gln Tyr Glu Ser Val Leu Met
465                 470                 475                 480 gtg tcc atc gac cag ctg ctg gac agc atg aag gaa atc ggc tcc aac      1488
Val Ser Ile Asp Gln Leu Leu Asp Ser Met Lys Glu Ile Gly Ser Asn
            485                 490                 495 tgc ctg aac aac gag ttc aac ttc ttc aag cgg cac atc tgc gac gcc      1536
Cys Leu Asn Asn Glu Phe Asn Phe Phe Lys Arg His Ile Cys Asp Ala
        500                 505                 510 aac aaa gaa ggc atg ttc ctg ttt aga gcc gcc aga aag ctg cgg cag      1584
Asn Lys Glu Gly Met Phe Leu Phe Arg Ala Ala Arg Lys Leu Arg Gln
    515                 520                 525 ttc ctg aag atg aac agc acc ggc gac ttc gac ctg cat ctg ctg aaa      1632
Phe Leu Lys Met Asn Ser Thr Gly Asp Phe Asp Leu His Leu Leu Lys
530                 535                 540 gtg tcc gag ggc acc acc atc ctg ctg aac tgt acc ggc caa gtg aag      1680
Val Ser Glu Gly Thr Thr Ile Leu Leu Asn Cys Thr Gly Gln Val Lys
545                 550                 555                 560 ggc aga aag cct gct gct ctg ggc gag gcc cag cct acc aag tcc ctg      1728
Gly Arg Lys Pro Ala Ala Leu Gly Glu Ala Gln Pro Thr Lys Ser Leu
            565                 570                 575 gaa gag aac aag agc ctg aaa gag cag aag aaa ctg aac gac ctg tgc      1776
Glu Glu Asn Lys Ser Leu Lys Glu Gln Lys Lys Leu Asn Asp Leu Cys
        580                 585                 590 ttc ctg aag cgg ctg ctg cag gaa atc aag acc tgc tgg aac aag att      1824
Phe Leu Lys Arg Leu Leu Gln Glu Ile Lys Thr Cys Trp Asn Lys Ile
    595                 600                 605 ctg atg ggc acc aaa gag cac tga                                      1848
Leu Met Gly Thr Lys Glu His
    610                 615

<210> SEQ ID NO 7
<211> LENGTH: 615
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Asn Ser Asp Asn Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Lys Tyr Ser Asn Ser Pro Gly Ala Phe Asp Ile
```

```
            100                 105                 110
Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Val Glu Pro Lys
            210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Ser Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys Gly Gly Gly Gly Ser Gly Gly Gly Gly Ser Asp
            450                 455                 460

Cys Asp Ile Glu Gly Lys Asp Gly Lys Gln Tyr Glu Ser Val Leu Met
465                 470                 475                 480

Val Ser Ile Asp Gln Leu Leu Asp Ser Met Lys Glu Ile Gly Ser Asn
                485                 490                 495

Cys Leu Asn Asn Glu Phe Asn Phe Phe Lys Arg His Ile Cys Asp Ala
                500                 505                 510

Asn Lys Glu Gly Met Phe Leu Phe Arg Ala Ala Arg Lys Leu Arg Gln
            515                 520                 525
```

```
Phe Leu Lys Met Asn Ser Thr Gly Asp Phe Asp Leu His Leu Leu Lys
        530                 535                 540

Val Ser Glu Gly Thr Thr Ile Leu Leu Asn Cys Thr Gly Gln Val Lys
545                 550                 555                 560

Gly Arg Lys Pro Ala Ala Leu Gly Glu Ala Gln Pro Thr Lys Ser Leu
                565                 570                 575

Glu Glu Asn Lys Ser Leu Lys Glu Gln Lys Lys Leu Asn Asp Leu Cys
            580                 585                 590

Phe Leu Lys Arg Leu Leu Gln Glu Ile Lys Thr Cys Trp Asn Lys Ile
        595                 600                 605

Leu Met Gly Thr Lys Glu His
        610                 615

<210> SEQ ID NO 8
<211> LENGTH: 648
<212> TYPE: DNA
<213> ORGANISM: Artificial Sequence
<220> FEATURE:
<223> OTHER INFORMATION: L-chain of fused form of anti-human CD73
      antibody and IL-7

<400> SEQUENCE: 8
gacatccaga tgacccagtc ccctccagc ctgtctgctt ccgtgggcga cagagtgacc      60
atcacctgtc gggcctccca gatcatcggc ccttggctgg cttggtatca gcagaagcct    120
ggcaaggccc ccaagctgct gatctacaga gcctcctccc tggaatccgg cgtgccctcc    180
agattctccg gctctggctc tggcaccgac tttaccctga ccatcagctc cctgcagccc    240
gaggacttcg ccacctacta ctgccagcag tacaactcct actcccccctg gaccttcggc    300 cagggcacca aggtggaaat caagcggacc gtggccgctc cctccgtgtt catcttccca    360
ccttccgacg agcagctgaa gtccggcacc gcttctgtcg tgtgcctgct gaacaacttc    420 taccccccgcg aggccaaggt gcagtggaag gtggacaacg ccctgcagtc cggcaactcc    480
caggaaagcg tgaccgagca ggactccaag gacagcacct actccctgtc ctccaccctg    540
accctgtcca aggccgacta cgagaagcac aaggtgtacg cctgcgaagt gacccaccag    600
ggcctgtcta gccccgtgac caagtctttc aaccggggcg agtgctag               648

<210> SEQ ID NO 9
<211> LENGTH: 1848
<212> TYPE: DNA
<213> ORGANISM: Artificial Sequence
<220> FEATURE:
<223> OTHER INFORMATION: H-chain of fused form of anti-human CD73
      antibody and IL-7 mutant
<220> FEATURE:
<221> NAME/KEY: CDS
<222> LOCATION: (1)..(1848)

<400> SEQUENCE: 9 gaa gtg cag ctg gtg gaa tct ggc ggc gga ctg gtg cag cct ggc gga      48
Glu Val Gln Leu Val Glu Ser Gly Gly Gly Leu Val Gln Pro Gly Gly
1               5                   10                  15 tct ctg aga ctg tct tgt gcc gcc tcc ggc ttc acc ttc gac gac tac      96
Ser Leu Arg Leu Ser Cys Ala Ala Ser Gly Phe Thr Phe Asp Asp Tyr
            20                  25                  30 gct atg cac tgg gtg cga cag gcc cct ggc aag gga ctg gaa tgg gtg     144
Ala Met His Trp Val Arg Gln Ala Pro Gly Lys Gly Leu Glu Trp Val
        35                  40                  45 tcc ggc atc aac tgg aac tcc gac aac atc gac tac gcc gac tcc gtg     192
```

```
Ser Gly Ile Asn Trp Asn Ser Asp Asn Ile Asp Tyr Ala Asp Ser Val
 50                  55                  60 aag ggc cgg ttc acc atc tcc cgg gac aac tcc aag aac acc ctg tac      240
Lys Gly Arg Phe Thr Ile Ser Arg Asp Asn Ser Lys Asn Thr Leu Tyr
 65                  70                  75                  80 ctg cag atg aac tcc ctg cgg gcc gag gac acc gcc gtg tac tac tgc      288
Leu Gln Met Asn Ser Leu Arg Ala Glu Asp Thr Ala Val Tyr Tyr Cys
                     85                  90                  95 gcc aag gac cgg cgg aag tac tcc aac tct cct ggc gcc ttc gac atc      336
Ala Lys Asp Arg Arg Lys Tyr Ser Asn Ser Pro Gly Ala Phe Asp Ile
                100                 105                 110 tgg ggc cag ggc aca ctc gtg acc gtg tcc tct gct tcc acc aag ggc      384
Trp Gly Gln Gly Thr Leu Val Thr Val Ser Ser Ala Ser Thr Lys Gly
            115                 120                 125 ccc tcc gtg ttt cct ctg gcc cct tcc agc aag tcc acc tct ggc gga      432
Pro Ser Val Phe Pro Leu Ala Pro Ser Ser Lys Ser Thr Ser Gly Gly
130                 135                 140 aca gcc gct ctg ggc tgc ctc gtg aag gac tac ttc ccc gag ccc gtg      480
Thr Ala Ala Leu Gly Cys Leu Val Lys Asp Tyr Phe Pro Glu Pro Val
145                 150                 155                 160 aca gtg tct tgg aac tct ggc gcc ctg act tct ggc gtg cac acc ttc      528
Thr Val Ser Trp Asn Ser Gly Ala Leu Thr Ser Gly Val His Thr Phe
                165                 170                 175 cct gct gtg ctg cag tct agc ggc ctg tac tcc ctg tcc tcc gtc gtg      576
Pro Ala Val Leu Gln Ser Ser Gly Leu Tyr Ser Leu Ser Ser Val Val
            180                 185                 190 act gtg ccc tcc agc tct ctg ggc acc cag acc tac atc tgc aac gtg      624
Thr Val Pro Ser Ser Ser Leu Gly Thr Gln Thr Tyr Ile Cys Asn Val
        195                 200                 205 aac cac aag ccc tcc aac acc aag gtg gac aag aag gtg gaa ccc aag      672
Asn His Lys Pro Ser Asn Thr Lys Val Asp Lys Lys Val Glu Pro Lys
210                 215                 220 tcc tgc gac aag acc cac acc tgt ccc cct tgt cct gcc cct gaa gct      720
Ser Cys Asp Lys Thr His Thr Cys Pro Pro Cys Pro Ala Pro Glu Ala
225                 230                 235                 240 gct ggc ggc cct tct gtg ttt ctg ttc ccc cca aag cct aag gac acc      768
Ala Gly Gly Pro Ser Val Phe Leu Phe Pro Pro Lys Pro Lys Asp Thr
                245                 250                 255 ctg atg atc tcc cgg acc ccc gaa gtg acc tgc gtg gtg gtg gat gtg      816
Leu Met Ile Ser Arg Thr Pro Glu Val Thr Cys Val Val Val Asp Val
            260                 265                 270 tcc cac gag gac cct gaa gtg aag ttc aat tgg tac gtg gac ggc gtg      864
Ser His Glu Asp Pro Glu Val Lys Phe Asn Trp Tyr Val Asp Gly Val
        275                 280                 285 gaa gtg cac aac gcc aag acc aag cct aga gag gaa cag tac aac tcc      912
Glu Val His Asn Ala Lys Thr Lys Pro Arg Glu Glu Gln Tyr Asn Ser
290                 295                 300 acc tac cgg gtg gtg tcc gtg ctg acc gtg ctg cat cag gac tgg ctg      960
Thr Tyr Arg Val Val Ser Val Leu Thr Val Leu His Gln Asp Trp Leu
305                 310                 315                 320 aac ggc aaa gag tac aag tgc aag gtg tcc aac aag gcc ctg ccc gcc     1008
Asn Gly Lys Glu Tyr Lys Cys Lys Val Ser Asn Lys Ala Leu Pro Ala
                325                 330                 335 tcc atc gaa aag acc atc tcc aag gcc aag ggc cag ccc cgg gaa ccc     1056
Ser Ile Glu Lys Thr Ile Ser Lys Ala Lys Gly Gln Pro Arg Glu Pro
            340                 345                 350 cag gtg tac aca ctg ccc cct agc agg gac gag ctg acc aag aac cag     1104
Gln Val Tyr Thr Leu Pro Pro Ser Arg Asp Glu Leu Thr Lys Asn Gln
        355                 360                 365
```

```
gtg tcc ctg acc tgt ctc gtg aaa ggc ttc tac ccc tcc gat atc gcc    1152
Val Ser Leu Thr Cys Leu Val Lys Gly Phe Tyr Pro Ser Asp Ile Ala
        370                 375                 380 gtg gaa tgg gag agc aac ggc cag ccc gag aac aac tat aag acc acc    1200
Val Glu Trp Glu Ser Asn Gly Gln Pro Glu Asn Asn Tyr Lys Thr Thr
385                 390                 395                 400 ccc cct gtg ctg gac tcc gac ggc tca ttc ttt ctg tac tcc aag ctg    1248
Pro Pro Val Leu Asp Ser Asp Gly Ser Phe Phe Leu Tyr Ser Lys Leu
                405                 410                 415 aca gtg gac aag tcc cgg tgg cag cag ggc aac gtg ttc tcc tgc agc    1296
Thr Val Asp Lys Ser Arg Trp Gln Gln Gly Asn Val Phe Ser Cys Ser
            420                 425                 430 gtg atg cac gag gcc ctg cac aac cac tac acc cag aag tcc ctg tcc    1344
Val Met His Glu Ala Leu His Asn His Tyr Thr Gln Lys Ser Leu Ser
        435                 440                 445 ctg tct ccc gga aaa ggc ggc gga gga tcc gga ggc gga tct gat        1392
Leu Ser Pro Gly Lys Gly Gly Gly Gly Ser Gly Gly Gly Gly Ser Asp
    450                 455                 460 tgt gac atc gag ggc aag gac ggc aag cag tac gag agc gtg ctg atg    1440
Cys Asp Ile Glu Gly Lys Asp Gly Lys Gln Tyr Glu Ser Val Leu Met
465                 470                 475                 480 gtg tcc atc gac cag ctg ctg gac agc atg aag gaa atc ggc tcc aac    1488
Val Ser Ile Asp Gln Leu Leu Asp Ser Met Lys Glu Ile Gly Ser Asn
                485                 490                 495 tgc ctg aac aac gag ttc aac ttc ttc aag cgg cac atc tgc gac gcc    1536
Cys Leu Asn Asn Glu Phe Asn Phe Phe Lys Arg His Ile Cys Asp Ala
            500                 505                 510 aac aaa gaa ggc atg ttc ctg ttt aga gcc gcc aga aag ctg cgg cag    1584
Asn Lys Glu Gly Met Phe Leu Phe Arg Ala Ala Arg Lys Leu Arg Gln
        515                 520                 525 ttc ctg aag atg aac agc acc ggc gac ttc gac ctg cat ctg ctg gcc    1632
Phe Leu Lys Met Asn Ser Thr Gly Asp Phe Asp Leu His Leu Leu Ala
    530                 535                 540 gtg tcc gag ggc acc acc atc ctg ctg aac tgt acc ggc caa gtg aag    1680
Val Ser Glu Gly Thr Thr Ile Leu Leu Asn Cys Thr Gly Gln Val Lys
545                 550                 555                 560 ggc aga aag cct gct gct ctg ggc gag gcc cag cct acc aag tcc ctg    1728
Gly Arg Lys Pro Ala Ala Leu Gly Glu Ala Gln Pro Thr Lys Ser Leu
                565                 570                 575 gaa gag aac aag agc ctg aaa gag cag aag aaa ctg aac gac ctg tgc    1776
Glu Glu Asn Lys Ser Leu Lys Glu Gln Lys Lys Leu Asn Asp Leu Cys
            580                 585                 590 ttc ctg aag cgg ctg ctg cag gaa atc gcc acc tgc tgg aac aag att    1824
Phe Leu Lys Arg Leu Leu Gln Glu Ile Ala Thr Cys Trp Asn Lys Ile
        595                 600                 605 ctg atg ggc acc aaa gag cac tga                                    1848
Leu Met Gly Thr Lys Glu His
    610                 615
```

<210> SEQ ID NO 10
<211> LENGTH: 615
<212> TYPE: PRT
<213> ORGANISM: Artificial Sequence
<220> FEATURE:
<223> OTHER INFORMATION: Synthetic Construct

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30
```

```
Ala Met His Trp Val Arg Gln Ala Pro Gly Lys Gly Leu Glu Trp Val
         35                  40                  45

Ser Gly Ile Asn Trp Asn Ser Asp Asn Ile Asp Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Arg Lys Tyr Ser Asn Ser Pro Gly Ala Phe Asp Ile
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Ser Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445
```

```
Leu Ser Pro Gly Lys Gly Gly Gly Ser Gly Gly Gly Ser Asp
    450                 455                 460

Cys Asp Ile Glu Gly Lys Asp Gly Lys Gln Tyr Glu Ser Val Leu Met
465                 470                 475                 480

Val Ser Ile Asp Gln Leu Leu Asp Ser Met Lys Glu Ile Gly Ser Asn
                485                 490                 495

Cys Leu Asn Asn Glu Phe Asn Phe Phe Lys Arg His Ile Cys Asp Ala
                500                 505                 510

Asn Lys Glu Gly Met Phe Leu Phe Arg Ala Ala Arg Lys Leu Arg Gln
                515                 520                 525

Phe Leu Lys Met Asn Ser Thr Gly Asp Phe Asp Leu His Leu Leu Ala
        530                 535                 540

Val Ser Glu Gly Thr Thr Ile Leu Leu Asn Cys Thr Gly Gln Val Lys
545                 550                 555                 560

Gly Arg Lys Pro Ala Ala Leu Gly Glu Ala Gln Pro Thr Lys Ser Leu
                565                 570                 575

Glu Glu Asn Lys Ser Leu Lys Glu Gln Lys Lys Leu Asn Asp Leu Cys
                580                 585                 590

Phe Leu Lys Arg Leu Leu Gln Glu Ile Ala Thr Cys Trp Asn Lys Ile
                595                 600                 605

Leu Met Gly Thr Lys Glu His
        610                 615

<210> SEQ ID NO 11
<211> LENGTH: 1362
<212> TYPE: DNA
<213> ORGANISM: Artificial Sequence
<220> FEATURE:
<223> OTHER INFORMATION: H-chain of fused form of anti-human CD73
      antibody and IL-21

<400> SEQUENCE: 11
gaagtgcagc tggtggaatc tggcggcgga ctggtgcagc ctggcggatc tctgagactg      60
tcttgtgccg cctccggctt caccttcgac gactacgcta tgcactgggt gcgacaggcc    120
cctggcaagg gactggaatg ggtgtccggc atcaactgga ctccgacaa catcgactac     180 gccgactccg tgaagggccg gttcaccatc tcccgggaca actccaagaa caccctgtac    240
ctgcagatga actccctgcg ggccgaggac accgccgtgt actactgcgc caaggaccgg    300
cggaagtact ccaactctcc tggcgccttc gacatctggg gccagggcac actcgtgacc    360
gtgtcctctg cttccaccaa gggcccctcc gtgtttcctc tggccccttc cagcaagtcc    420
acctctggcg aacagccgc tctgggctgc ctcgtgaagg actacttccc cgagccgtg     480 acagtgtctt ggaactctgg cgccctgact tctggcgtgc acccttccc tgctgtgctg    540 cagtctagcg gcctgtactc cctgtcctcc gtcgtgactg tgccctccag ctctctgggc    600
acccagacct acatctgcaa cgtgaaccac aagccctcca caccaaggt ggacaagaag     660 gtggaaccca gtcctgcga caagacccac acctgtcccc cttgtcctgc ccctgaagct    720
gctggcggcc cttctgtgtt tctgttcccc ccaaagccta aggacaccct gatgatctcc    780 cggaccccg aagtgacctg cgtggtggtg gatgtgtccc acgaggaccc tgaagtgaag    840
ttcaattggt acgtggacgg cgtggaagtg cacaacgcca agaccaagcc tagagaggaa    900
cagtacaact ccacctaccg ggtggtgtcc gtgctgaccg tgctgcatca ggactggctg    960
aacggcaaaa gtacaagtg caaggtgtcc aacaaggccc tgcccgcctc catcgaaaag    1020
accatctcca aggccaaggg ccagccccgg gaacccagg tgtacacact gcccccctagc   1080
```

```
agggacgagc tgaccaagaa ccaggtgtcc ctgacctgtc tcgtgaaagg cttctacccc    1140
tccgatatcg ccgtggaatg ggagagcaac ggccagccg agaacaacta taagaccacc    1200 cccctgtgc tggactccga cggctcattc tttctgtact ccaagctgac agtggacaag    1260
tcccggtggc agcagggcaa cgtgttctcc tgcagcgtga tgcacgaggc cctgcacaac    1320
cactacaccc agaagtccct gtccctgagc cccggcaagt ga                       1362
```

```
<210> SEQ ID NO 12
<211> LENGTH: 1077
<212> TYPE: DNA
<213> ORGANISM: Artificial Sequence
<220> FEATURE:
<223> OTHER INFORMATION: L-chain of fused form of anti-human CD73
      antibody and IL-21
<220> FEATURE:
<221> NAME/KEY: CDS
<222> LOCATION: (1)..(1077)

<400> SEQUENCE: 12
```

```
gat atc cag atg aca cag tct cct agt tcc ttg tcc gct agc gtt ggt     48
Asp Ile Gln Met Thr Gln Ser Pro Ser Ser Leu Ser Ala Ser Val Gly
1               5                   10                  15 gac cgt gtg acc ata acc tgt cga gct agc cag att att ggg cca tgg    96
Asp Arg Val Thr Ile Thr Cys Arg Ala Ser Gln Ile Ile Gly Pro Trp
                20                  25                  30 ctt gcc tgg tat cag cag aag cct ggt aaa gca ccc aag ctc ctc atc   144
Leu Ala Trp Tyr Gln Gln Lys Pro Gly Lys Ala Pro Lys Leu Leu Ile
            35                  40                  45 tat aga gcc agc tct ctg gaa tcc ggg gtg cca tca cgg ttc tct gga   192
Tyr Arg Ala Ser Ser Leu Glu Ser Gly Val Pro Ser Arg Phe Ser Gly
        50                  55                  60 tct ggc tct ggc acc gac ttt acc ctg aca att tcc tcc ctt caa ccc   240
Ser Gly Ser Gly Thr Asp Phe Thr Leu Thr Ile Ser Ser Leu Gln Pro
65                  70                  75                  80 gag gac ttt gcc aca tac tac tgc cag cag tac aac tcc tac agt ccc   288
Glu Asp Phe Ala Thr Tyr Tyr Cys Gln Gln Tyr Asn Ser Tyr Ser Pro
                85                  90                  95 tgg acc ttt ggc caa ggc acc aaa gtg gag atc aag cgc acc gta gct   336
Trp Thr Phe Gly Gln Gly Thr Lys Val Glu Ile Lys Arg Thr Val Ala
                100                 105                 110 gcc cct tcc gtg ttc atc ttt cca cca agt gat gaa cag ctc aag tca   384
Ala Pro Ser Val Phe Ile Phe Pro Pro Ser Asp Glu Gln Leu Lys Ser
            115                 120                 125 ggg act gcc tct gtt gta tgc ctg ctc aat aac ttc tat ccc aga gaa   432
Gly Thr Ala Ser Val Val Cys Leu Leu Asn Asn Phe Tyr Pro Arg Glu
        130                 135                 140 gcc aag gtc caa tgg aag gtg gac aat gct ctg cag tct ggg aat agc   480
Ala Lys Val Gln Trp Lys Val Asp Asn Ala Leu Gln Ser Gly Asn Ser
145                 150                 155                 160 cag gaa tcc gtt act gag caa gat tcc aaa gac tcc act tac tcc ttg   528
Gln Glu Ser Val Thr Glu Gln Asp Ser Lys Asp Ser Thr Tyr Ser Leu
                165                 170                 175 tca tct aca ctg acc ctc tca aaa gca gac tac gaa aag cac aaa gtg   576
Ser Ser Thr Leu Thr Leu Ser Lys Ala Asp Tyr Glu Lys His Lys Val
                180                 185                 190 tat gcc tgt gag gtc aca cac caa ggc ctc agc agt ccc gtc acc aag   624
Tyr Ala Cys Glu Val Thr His Gln Gly Leu Ser Ser Pro Val Thr Lys
            195                 200                 205 agc ttc aac aga ggg gag tgt ggc ggt gga gga tcc gga ggc ggt ggc   672
Ser Phe Asn Arg Gly Glu Cys Gly Gly Gly Gly Ser Gly Gly Gly Gly
```

```
                210                 215                 220
agt cag gga cag gat cgc cac atg atc cgt atg agg caa ctg att gat    720
Ser Gln Gly Gln Asp Arg His Met Ile Arg Met Arg Gln Leu Ile Asp
225                 230                 235                 240 atc gtt gac cag ctg aag aac tac gtg aac gat ctt gtc ccc gag ttt    768
Ile Val Asp Gln Leu Lys Asn Tyr Val Asn Asp Leu Val Pro Glu Phe
                245                 250                 255 ctt cct gct cct gag gac gtg gag aca aac tgt gaa tgg agc gca ttt    816
Leu Pro Ala Pro Glu Asp Val Glu Thr Asn Cys Glu Trp Ser Ala Phe
            260                 265                 270 tcc tgc ttc cag aaa gca cag ctg aaa tct gct aat acg ggc aat aac    864
Ser Cys Phe Gln Lys Ala Gln Leu Lys Ser Ala Asn Thr Gly Asn Asn
        275                 280                 285 gag cgg ata atc aac gtg tca atc aag aaa ctg aaa cgc aaa cct cca    912
Glu Arg Ile Ile Asn Val Ser Ile Lys Lys Leu Lys Arg Lys Pro Pro
    290                 295                 300 tca acg aat gca ggg agg cga cag aag cat agg ctg aca tgt ccc tct    960
Ser Thr Asn Ala Gly Arg Arg Gln Lys His Arg Leu Thr Cys Pro Ser
305                 310                 315                 320 tgc gac tcc tat gag aag aag cct ccc aag gag ttc ttg gaa cga ttc   1008
Cys Asp Ser Tyr Glu Lys Lys Pro Pro Lys Glu Phe Leu Glu Arg Phe
                325                 330                 335 aag agt ttg ctg cag aag atg att cac cag cat ctg agt agc cgg act   1056
Lys Ser Leu Leu Gln Lys Met Ile His Gln His Leu Ser Ser Arg Thr
            340                 345                 350 cat gga agc gaa gat agc tga                                        1077
His Gly Ser Glu Asp Ser
        355

<210> SEQ ID NO 13
<211> LENGTH: 358
<212> TYPE: PRT
<213> ORGANISM: Artificial Sequence
<220> FEATURE:
<223> OTHER INFORMATION: Synthetic Construct

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Gly Pro Trp
            20                  25                  30

Leu Ala Trp Tyr Gln Gln Lys Pro Gly Lys Ala Pro Lys Leu Leu Ile
        35                  40                  45

Tyr Arg Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
```

```
                165                 170                 175
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys Gly Gly Gly Ser Gly Gly Gly Gly
            210                 215                 220

Ser Gln Gly Gln Asp Arg His Met Ile Arg Met Arg Gln Leu Ile Asp
225                 230                 235                 240

Ile Val Asp Gln Leu Lys Asn Tyr Val Asn Asp Leu Val Pro Glu Phe
            245                 250                 255

Leu Pro Ala Pro Glu Asp Val Glu Thr Asn Cys Glu Trp Ser Ala Phe
            260                 265                 270

Ser Cys Phe Gln Lys Ala Gln Leu Lys Ser Ala Asn Thr Gly Asn Asn
            275                 280                 285

Glu Arg Ile Ile Asn Val Ser Ile Lys Lys Leu Lys Arg Lys Pro Pro
            290                 295                 300

Ser Thr Asn Ala Gly Arg Arg Gln Lys His Arg Leu Thr Cys Pro Ser
305                 310                 315                 320

Cys Asp Ser Tyr Glu Lys Lys Pro Pro Lys Glu Phe Leu Glu Arg Phe
            325                 330                 335

Lys Ser Leu Leu Gln Lys Met Ile His Gln His Leu Ser Ser Arg Thr
            340                 345                 350

His Gly Ser Glu Asp Ser
            355

<210> SEQ ID NO 14
<211> LENGTH: 1077
<212> TYPE: DNA
<213> ORGANISM: Artificial Sequence
<220> FEATURE:
<223> OTHER INFORMATION: L-chain of fused form of anti-human CD73
      antibody and IL-21 mutant
<220> FEATURE:
<221> NAME/KEY: CDS
<222> LOCATION: (1)..(1077)

<400> SEQUENCE: 14 gat atc cag atg aca cag tct cct agt tcc ttg tcc gct agc gtt ggt        48
Asp Ile Gln Met Thr Gln Ser Pro Ser Ser Leu Ser Ala Ser Val Gly
1               5                   10                  15 gac cgt gtg acc ata acc tgt cga gct agc cag att att ggg cca tgg       96
Asp Arg Val Thr Ile Thr Cys Arg Ala Ser Gln Ile Ile Gly Pro Trp
                20                  25                  30 ctt gcc tgg tat cag cag aag cct ggt aaa gca ccc aag ctc ctc atc      144
Leu Ala Trp Tyr Gln Gln Lys Pro Gly Lys Ala Pro Lys Leu Leu Ile
            35                  40                  45 tat aga gcc agc tct ctg gaa tcc ggg gtg cca tca cgg ttc tct gga      192
Tyr Arg Ala Ser Ser Leu Glu Ser Gly Val Pro Ser Arg Phe Ser Gly
        50                  55                  60 tct ggc tct ggc acc gac ttt acc ctg aca att tcc tcc ctt caa ccc      240
Ser Gly Ser Gly Thr Asp Phe Thr Leu Thr Ile Ser Ser Leu Gln Pro
65                  70                  75                  80 gag gac ttt gcc aca tac tac tgc cag cag tac aac tcc tac agt ccc      288
Glu Asp Phe Ala Thr Tyr Tyr Cys Gln Gln Tyr Asn Ser Tyr Ser Pro
                85                  90                  95 tgg acc ttt ggc caa ggc acc aaa gtg gag atc aag cgc acc gta gct      336
Trp Thr Phe Gly Gln Gly Thr Lys Val Glu Ile Lys Arg Thr Val Ala
            100                 105                 110
```

```
gcc cct tcc gtg ttc atc ttt cca cca agt gat gaa cag ctc aag tca    384
Ala Pro Ser Val Phe Ile Phe Pro Pro Ser Asp Glu Gln Leu Lys Ser
        115                 120                 125 ggg act gcc tct gtt gta tgc ctg ctc aat aac ttc tat ccc aga gaa    432
Gly Thr Ala Ser Val Val Cys Leu Leu Asn Asn Phe Tyr Pro Arg Glu
130                 135                 140 gcc aag gtc caa tgg aag gtg gac aat gct ctg cag tct ggg aat agc    480
Ala Lys Val Gln Trp Lys Val Asp Asn Ala Leu Gln Ser Gly Asn Ser
145                 150                 155                 160 cag gaa tcc gtt act gag caa gat tcc aaa gac tcc act tac tcc ttg    528
Gln Glu Ser Val Thr Glu Gln Asp Ser Lys Asp Ser Thr Tyr Ser Leu
                165                 170                 175 tca tct aca ctg acc ctc tca aaa gca gac tac gaa aag cac aaa gtg    576
Ser Ser Thr Leu Thr Leu Ser Lys Ala Asp Tyr Glu Lys His Lys Val
            180                 185                 190 tat gcc tgt gag gtc aca cac caa ggc ctc agc agt ccc gtc acc aag    624
Tyr Ala Cys Glu Val Thr His Gln Gly Leu Ser Ser Pro Val Thr Lys
        195                 200                 205 agc ttc aac aga ggg gag tgt ggc ggt gga gga tcc gga ggc ggt ggc    672
Ser Phe Asn Arg Gly Glu Cys Gly Gly Gly Gly Ser Gly Gly Gly Gly
    210                 215                 220 agt cag gga cag gat cgc cac atg atc cgt atg agg caa ctg att gat    720
Ser Gln Gly Gln Asp Arg His Met Ile Arg Met Arg Gln Leu Ile Asp
225                 230                 235                 240 atc gtt gac cag ctg aag aac tac gtg aac gat ctt gtc ccc gag ttt    768
Ile Val Asp Gln Leu Lys Asn Tyr Val Asn Asp Leu Val Pro Glu Phe
                245                 250                 255 ctt cct gct cct gag gac gtg gag aca aac tgt gaa tgg agc gca ttt    816
Leu Pro Ala Pro Glu Asp Val Glu Thr Asn Cys Glu Trp Ser Ala Phe
            260                 265                 270 tcc tgc ttc cag aaa gca cag ctg aaa tct gct aat acg ggc aat aac    864
Ser Cys Phe Gln Lys Ala Gln Leu Lys Ser Ala Asn Thr Gly Asn Asn
        275                 280                 285 gag cgg ata atc aac gtg tca atc aag aaa ctg aaa gcc aaa cct cca    912
Glu Arg Ile Ile Asn Val Ser Ile Lys Lys Leu Lys Ala Lys Pro Pro
    290                 295                 300 tca acg aat gca ggg agg cga cag aag cat agg ctg aca tgt ccc tct    960
Ser Thr Asn Ala Gly Arg Arg Gln Lys His Arg Leu Thr Cys Pro Ser
305                 310                 315                 320 tgc gac tcc tat gag aag aag cct ccc aag gag ttc ttg gaa cga ttc   1008
Cys Asp Ser Tyr Glu Lys Lys Pro Pro Lys Glu Phe Leu Glu Arg Phe
                325                 330                 335 aag agt ttg ctg cag aag atg att cac cag cat ctg agt agc cgg act   1056
Lys Ser Leu Leu Gln Lys Met Ile His Gln His Leu Ser Ser Arg Thr
            340                 345                 350 cat gga agc gaa gat agc tga                                       1077
His Gly Ser Glu Asp Ser
        355

<210> SEQ ID NO 15
<211> LENGTH: 358
<212> TYPE: PRT
<213> ORGANISM: Artificial Sequence
<220> FEATURE:
<223> OTHER INFORMATION: Synthetic Construct

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Gly Pro Trp
```

```
            20                  25                  30
Leu Ala Trp Tyr Gln Gln Lys Pro Gly Lys Ala Pro Lys Leu Leu Ile
         35                  40                  45

Tyr Arg Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Ser Pro
                 85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Gly Gly Gly Gly
    210                 215                 220

Ser Gln Gly Gln Asp Arg His Met Ile Arg Met Arg Gln Leu Ile Asp
225                 230                 235                 240

Ile Val Asp Gln Leu Lys Asn Tyr Val Asn Asp Leu Val Pro Glu Phe
                245                 250                 255

Leu Pro Ala Pro Glu Asp Val Glu Thr Asn Cys Glu Trp Ser Ala Phe
            260                 265                 270

Ser Cys Phe Gln Lys Ala Gln Leu Lys Ser Ala Asn Thr Gly Asn Asn
        275                 280                 285

Glu Arg Ile Ile Asn Val Ser Ile Lys Lys Leu Lys Ala Lys Pro Pro
    290                 295                 300

Ser Thr Asn Ala Gly Arg Arg Gln Lys His Arg Leu Thr Cys Pro Ser
305                 310                 315                 320

Cys Asp Ser Tyr Glu Lys Lys Pro Pro Lys Glu Phe Leu Glu Arg Phe
                325                 330                 335

Lys Ser Leu Leu Gln Lys Met Ile His Gln His Leu Ser Ser Arg Thr
            340                 345                 350

His Gly Ser Glu Asp Ser
        355

<210> SEQ ID NO 16
<211> LENGTH: 1848
<212> TYPE: DNA
<213> ORGANISM: Artificial Sequence
<220> FEATURE:
<223> OTHER INFORMATION: H-chain of fused form of anti-human CD73
      antibody and IL-7 mutant

<400> SEQUENCE: 16
gaagtacagt tggtcgaaag cggaggaggg ctggttcagc ctggcggctc actcagactg        60
tcatgcgctg cctctgggtt tacattcgac gattatgcca tgcattgggt acgacaggca       120
```

```
ccaggcaaag ggctggagtg ggtttctggg attaactgga atagcgataa tatcgactat    180
gccgactctg taaaggggcg ctttactatc agtcgggaca atagtaagaa tacgctctat    240
ctgcagatga atagcctgag agcagaagat accgctgtgt actactgtgc caaagaccgg    300
cgtaagtaca gtaactctcc tggtgccttt gacatctggg gacagggcac tcttgttacc    360
gtgagcagcg catctaccaa aggtccctca gtctttcccc tcgctcctag ttctaagtcc    420
acatcaggtg gaactgccgc tttggggttgc ctggtaaagg actactttcc cgagcctgtt    480
acagtgagct ggaactccgg agctctgaca tccggtgtgc acacatttcc tgccgttctt    540
cagtcctcag ggctgtattc cttgtcctca gtggttacag tgcccagcag tagtctgggg    600
acacagacat acatttgcaa tgtgaatcac aagccaagta acactaaggt cgataagaag    660
gtcgagccca aagttgcga taagacccat acttgtccac cttgtcctgc tcctgaggcc    720
gcaggaggcc cttctgtgtt cctgtttcca cccaaaccca aggacactct gatgattagc    780
cggacgccag aggtgacctg tgttgtggtt gatgtctctc acgaggaccc agaagtgaaa    840
ttcaactggt acgtcgacgg cgtggaagtg cacaatgcca aaaccaagcc acgcgaggag    900
cagtacaaca gcacctatcg ggtggtgagc gtgttgactg tgctgcatca agattggctg    960
aatggaaagg agtacaagtg taaggtgtct aacaaggcac tgcccgcaag catcgaaaag   1020
accatcagta aggctaaggg ccagcccagg gaaccacagg tctacaccct gccaccttcc   1080
cgtgacgagt tgaccaagaa ccaggtgtca cttacgtgct tggtgaaagg cttctatccc   1140
tccgacattg ccgtagaatg ggaaagcaat gggcaacccg agaataacta caaaacaact   1200
ccacccgtcc ttgattctga cggttccttc ttcctctatt ccaaactgac tgtcgataaa   1260
tctcgatggc aacagggcaa tgtcttttct tgtagtgtga tgcatgaagc attgcataac   1320
cactacaccc agaagtccct gtctttgtcc cctgggaaag gaggcggtgg atccggtggt   1380
ggcggctcag attgcgacat agaaggcaag gacggcaaac agtatgagtc cgtcctgatg   1440
gtgtccattg atcagctgct ggattctatg aaggaaatcg gaagcaactg cctgaacaat   1500
gagtttaact tcttcaaacg acacatctgt gatgccaaca agagggcat gtttctcttc   1560
agagccgcta ggaaactgag gcagtttctc aagatgaact ccactggcga cttcgatctg   1620
caccttctgg ccgtatcaga ggggaccaca atactgctga actgcaccgg ccaagtcaag   1680
ggtcgcaagc ccgctgccct tggagaagct caacccacca aaagcctgga agagaacaaa   1740
tccctcaagg agcagaagaa actcaacgac ctgtgctttc tcaagaggct ccttcaggag   1800
attgccacct gttggaataa gatccttatg gggacaaaag agcactga               1848
```